(12) United States Patent
Thurkauf et al.

(10) Patent No.: US 6,358,955 B1
(45) Date of Patent: *Mar. 19, 2002

(54) SUBSTITUTED IMIDAZOLES AS SUBTYPE SPECIFIC DOPAMINE RECEPTOR LIGANDS AND PHARMACEUTICAL COMPOSITIONS CONTAINING SUCH SUBSTITUTED IMIDAZOLE

(75) Inventors: Andrew Thurkauf, Danbury; Raymond F. Horvath, North Branford; Jun Yuan, Clinton; John M. Peterson, New Haven, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/497,988

(22) Filed: Feb. 4, 2000

Related U.S. Application Data

(63) Continuation of application No. 08/859,861, filed on May 21, 1997, now Pat. No. 6,069,251, which is a continuation of application No. 08/462,833, filed on Jun. 5, 1995, now Pat. No. 5,633,377, which is a continuation of application No. 08/344,154, filed on Nov. 23, 1994, now abandoned, which is a continuation-in-part of application No. 08/081,317, filed on Nov. 8, 1993, now Pat. No. 5,428,164, which is a continuation-in-part of application No. 07/635,256, filed on Dec. 28, 1990, now Pat. No. 5,159,083.

(51) Int. Cl.[7] .................... A61K 31/454; A61K 31/496; A61K 31/506; A61N 25/18; A61N 25/24
(52) U.S. Cl. .................. 514/252.13; 514/269; 514/341; 514/395; 514/400; 544/295; 544/360; 544/364; 544/370; 546/193; 546/194; 546/210; 548/315.1; 548/335.5; 548/340.1; 548/343.1; 548/343.5
(58) Field of Search .................. 544/295, 360, 544/364, 370; 546/193, 194, 210; 548/315.1, 335.5, 340.1, 343.1, 343.5; 514/269, 395, 400, 252.13, 341

(56) References Cited

U.S. PATENT DOCUMENTS

| | | | | |
|---|---|---|---|---|
| 5,159,083 A | * | 10/1992 | Thurkauf et al. | 548/335.5 |
| 5,428,164 A | * | 6/1995 | Thurkauf et al. | 544/295 |
| 5,633,376 A | * | 5/1997 | Thurkauf et al. | 544/360 |
| 5,633,377 A | * | 5/1997 | Thurkauf et al. | 544/370 |
| 5,646,279 A | * | 7/1997 | Thurkauf et al. | 544/295 |
| 5,646,280 A | * | 7/1997 | Thurkauf et al. | 544/295 |
| 5,646,281 A | * | 7/1997 | Thurkauf et al. | 544/295 |
| 5,656,762 A | * | 8/1997 | Thurkauf et al. | 544/370 |
| 5,681,956 A | * | 10/1997 | Thurkauf et al. | 544/295 |
| 5,712,392 A | * | 1/1998 | Thurkauf et al. | 544/295 |
| 6,069,251 A | * | 5/2000 | Thurkauf et al. | 544/295 |

* cited by examiner

*Primary Examiner*—Floyd D. Higel
(74) *Attorney, Agent, or Firm*—McDonnell Boehnen Hulbert & Berghoff; Steven J. Sarussi

(57) ABSTRACT

Disclosed are compounds of the formula:

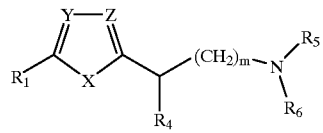

wherein $R_1$ represents optionally substituted aryl, heteroaryl, arylalkyl, or cycloalkyl groups; X, Z, and Y are optionally substituted nitrogen or carbon atoms; $R_3$ and $R_4$ are organic or inorganic substituents which may together form ring structures; m is zero, one or two; and $R_5$ and $R_6$ are are organic or inorganic substituents;

and the pharmaceutically acceptable addition salts thereof, which compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism.

21 Claims, 3 Drawing Sheets

Compound 1

Compound 8

Compound 16

Compound 19

Compound 20

Compound 21

Compound 22

Compound 23

Compound 24

Compound 25

Compound 26

Compound 43

Compound 45

Compound 47

Compound 50

Compound 52

Compound 55

Compound 56

Compound 58

Compound 60

Compound 61

Compound 65

SUBSTITUTED IMIDAZOLES AS SUBTYPE SPECIFIC DOPAMINE RECEPTOR LIGANDS AND PHARMACEUTICAL COMPOSITIONS CONTAINING SUCH SUBSTITUTED IMIDAZOLE

This application is a continuation of U.S. patent application Ser. No. 08/859,861, filed May 21, 1997, now U.S. Pat. No. 6,069,251; which is a continuation of U.S. patent application Ser. No. 08/462,833 filed Jun. 5, 1995, now U.S. Pat. No. 5,633,377; which is a continuation of U.S. patent application Ser. No. 08/344,154, filed Nov. 23, 1994, now abandoned; which is a continuation-in-part of U.S. patent application Ser. No. 08/081,317, filed Nov. 8, 1993, now U.S. Pat. No. 5,428,164; which is a which is a continuation-in-part of U.S. patent application Ser. No. 07/635,256, filed Dec. 28, 1990, now U.S. Pat. No. 5,159,083.

BACKGROUND OF THE INVENTION

1. Field of the Invention

This invention relates to certain 4-aminomethyl-2-substituted imidazole and 2-aminomethyl-4-substituted derivatives which selectively bind to brain dopamine receptor subtypes. This invention also relates to pharmaceutical compositions comprising such compounds. It further relates to the use of such compounds in treating affective disorders such as schizophrenia and depression as well as certain movement disorders such as Parkinsonism. Furthermore, compounds of this invention may be useful in treating the extrapyrimidyl side effects associated with the use of conventional neuroleptic agents. The interaction of these aminomethylimidazole derivatives of the invention with dopamine receptor subtypes is described. This interaction results in the pharmacological activities of these compounds.

2. Description of the Related Art

Schizophrenia or psychosis is a term used to describe a group of illnesses of unknown origin which affect approximately 2.5 million people in the United States. These disorders of the brain are characterized by a variety of symptoms which are classified as positive symptoms (disordered thought, hallucinations and delusions) and negative symptoms (social withdrawal and unresponsiveness). These disorders have an age of onset in adolescence or early adulthood and persist for many year The disorders tend to become more severe during the patient's lifetime and can result in prolonged institutionalization. In the United States today, approximately 40% of all hospitalized psychiatric patents suffer from schizophrenia.

During the 1950's physicians demonstrated that they could successfully treat psychotic patients with medications called neuroleptics; this classification of antipsychotic medication was based largely on the activating (neuroleptic) properties of the nervous system by these drugs. Subsequently, neuroleptic agents were shown to increase the concentrations of dopamine metabolites in the brain suggesting altered neuronal firing of the dopamine system. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia.

One of the major actions of antipsychotic medication is the blockade of dopamine receptors in brain. Several dopamine systems appear to exist in the brain and at least five classes of dopamine receptors appear to mediate the actions of this transmitter. These dopamine receptors differ in their pharmacological specificity and were originally classified upon these differences in the pharmacology of different chemical series. Butyrophenones, containing many potent antipsychotic drugs were quite weak at the dopamine receptor that activated adenylate cyclase (now known as a D1 dopamine receptor). In contrast, they labelled other dopamine receptors (called D2 receptors) in the subnanomolar range and a third type D3 in the nanomolar range. Two additional receptor subtypes have also been identified. D5 which is somewhat similar to D1 receptor type and D4 which is closely related to D3 and D2 receptor types. Phenothiazines possess nanomolar affinity for all three types of dopamine receptors. Other drugs have been developed with great specificity for the D1 subtype receptor and for the D2 subtype receptor.

A certain group of drugs (such as sulpiride and clozapine) have been developed with a lesser incidence of extrapyrimidyl side effects than classical neuroleptics. In addition, there is some indication that they may be more beneficial in treating negative symptoms in some patients. Drugs of this class are often referred to as atypical antipsychotic agents. Since all D2 blockers do not possess a similar profile, hypotheses underlying the differences have been investigated. The major differences have been in the anticholinergic actions of the neuroleptics as well as the possibility that the dopamine receptors may differ in motor areas from those in the limbic areas thought to mediate the antipsychotic responses. The existence of the D3, D4 and D5 and other as yet undiscovered dopamine receptors may contribute to this profile. Some of the atypical compounds possess similar activity at D2, D3 and D4 receptors. The examples of this patent fall into this general class of molecules.

Using molecular biological techniques it has been possible to clone cDNAs coding for each of the pharmacologically defined receptors. There are at least two forms of D1-type receptors which have been classified as D1 and D5, and two forms of D2-type receptors, classified now as D2 and D4 dopamine receptors. In addition, there is at least one form of D3 dopamine receptor. Examples from the substituted aminomethylimidazole series of this patent possess differential affinities for each receptor subtype.

Schizophrenia is characterized by a variety of cognitive dysfunctions; schizophrenic patients perform less well than other groups on most cognitive or attentional tasks. The positive and negative symptom dimensions of schizophrenia are also associated with distinct cognitive deficits. In general, positive symptoms (disordered thought processes, hallucinations and decisions) are related to auditory processing impairments including deficits in verbal memory and language comprehension. Negative symptoms (social withdrawal and unresponsiveness) are related more to visual/motor dysfunctions including poorer performance on visual memory, motor speed and dexterity tasks.

These disorders have an age of onset in adolescence or early adulthood and persist for many years. The interaction of frontal and septo-hippocampal brain systems, and failures of information processing and self monitoring have been theorized as the basis of positive symptoms. Negative symptoms are thought to arise from abnormalities in the interactions of frontal and striatal systems. Since cognitive disturbances are present in most of the patients diagnosed as having schizophrenia, it has been theorized that to understand the pathogenesis and etiology of schizophrenia one must understand the basic dysfunction of the cognitive disorder.

The cognitive disturbances found in schizophrenia include, but are not limited to, various verbal and visual memory deficits. There are various neurocognitive tasks for both animals and humans that have been developed to assess memory deficits, as well as memory enhancements, of various treatments. Many of the neurocognitive behavioral tasks are modulated or mediated by eural activity within the hippocampal brain system noted above.

Drug substances that interact with the hippocampus are capable of modulating memory in animals. Certain memory paradigms employed in animals have construct and predictive validity for memory assessment in humans. In animals (rodents), paradigms such as the Step-Down Passive Avoidance Task assay or the Spatial Water Maze Task assay reliably detect deficits produced by certain drugs in humans. For example, commonly prescribed benzodiazepine anxiolytics and sedative hypnotics are known to produce memory impairment in humans, including varying degrees of anterogade amnesia (depending on the exact drug). In the step-down passive avoidance paradigm these very same drugs disrupt the memory of animals given the compounds during the information acquisition or processing period. Likewise, benzodiazepines disrupt information processing and memories in the spatial water maze task in rodents. Thus, these animal models can be used to predict the memory impairing effects of certain compounds in humans. Conversely, these same animal models can predict the memory improving or enhancing effects of compounds in humans. Although fewer in number, drugs that improve memory in humans (e.g., Nootroprice, Beta carbolines) produce memory enhancing effects in rats in these models. Therefore, the spatial water maze and step-down passive avoidance paradigms in rodents are useful in predicting memory impairing and memory enhancing effects of test compounds in humans.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore compounds of this invention may be useful in treating the extrapyramidyl side effects associated with the use of conventional neuroleptic agents. Since dopamine D3 and D4 receptor subtypes are particularly concentrated in the limbic system (Taubes, *Science* (1994) 265, 1034) which controls cognition and emotion, compounds which interact with these receptors may have utility in the treatment of cognitive disorders. Such disorders may be the cognitive deficits which are a significant component of the negative symptoms (social withdrawal, and unresponsiveness) of schizophrenia. Other disorders involving memory impairment or attention deficit disorders may also be treated with some of the compounds of this invention that interact specifically with dopamine D3 and/or D4 receptor subtypes. Accordingly, the invention is directed to a compound of Formula I:

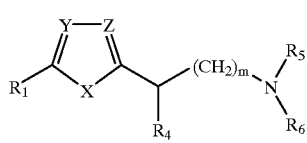

where $R_1$ is: aryl, heteroaryl arylalkyl, cycloalkyl or naphthyl: unsubstituted or substituted by up to 3 substituents which may be the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$;

X is: N or $NR_2$ where $R_2$ is hydrogen or straight or branched chain lower alkyl having 1–6 carbon atoms.

Y is: N or $CR_3$

Z is: $CR_3$ or N provided that Y and Z are not both $CR_3$; and provided that Y and Z are not both N;

$R_3$ is: hydrogen, lower alkyl, halogen, hydroxy lower alkyl or phenyl unsubstituted or substituted by up to three substituents which may be the same or different and represent hydrogen, halogen, trifluoromethyl, cyano, sulfonamido, hydroxy, straight or branched chain lower alkyl having 1–6 carbon atoms, or straight or branched chain lower alkoxy having 1–6 carbon atoms;

$R_4$ is: hydrogen or straight or branched chain lower alkyl having 1–6 carbon atoms, or $R_3$ and $R_4$ together may represent —$(CH_2)_{n1}$— where n1 is 2, 3 or 4; or $R_2$ and $R_4$ together may represent —$(CH_2)_{n2}$— where n2 is 2, 3 or 4.

m is: zero, one or two $R_5$ and $R_6$ are the same or different and represent hydrogen, straight or branched chain lower alkyl having 1–6 carbon atoms, aryl, straight or branched chain lower alkyl having 1–6 carbon atoms or $R_2$ and $R_5$ together may represent —$(CH_2)_{n3}$— where n3 is 2 or 3; or $NR_5R_6$ together represent: 2-(1,2,3,4tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_5R_6$ represents:

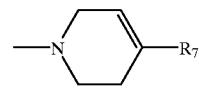

where $R_7$ is phenyl, benzyl or phenethyl with the phenyl ring unsubstituted or substituted with up to three substituents which may be the same or different and represent hydrogen, halogen, trifluoromethyl, hydroxy, straight or branched chain lower alkyl having 1–6 carbon atoms, or straight or branched chain lower alkoxy having 1–6 carbon atoms; or $R_5R_6$ represents:

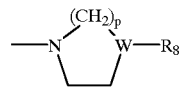

where p is 1, 2, or 3;

W is N or CH; and

W is N and $R_8$ is hydrogen, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or W is CH and $R_8$ is optionally substituted phenyl or an arylalkyl group such as, for example, phenylalkyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

These compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism. Furthermore, compounds of this invention may be useful in treating the extrapyramidyl side effects associated with the use of conventional neuroleptic agents. Furthermore, compounds of this invention may have utility in the treatment of cognitive disorders. Such disorders may be the cognitive deficits which are a significant component of the negative symptoms (social withdrawal, and unresponsiveness) of schizophrenia or other disorders involving memory impairment or attention deficit disorders.

The compounds of the invention, such as, for example, 2-Phenyl-4(5)-[(4-(2-pyrimidinyl)-piperazin-1-yl)-methyl]-imidazole dihydrochloride (compound 23), 2-Phenyl-4(5)-[(4-(2-pyridyl)-piperazin-1-yl)-methyl]-imidazole dihydrochloride (Compound 24), and 2-Phenyl-4(5)-[(4-phenyl-piperazin-1-yl)-methyl]-imidazole dihydrochloride (Compound 45), are antagonists binding to dopamine D4 receptors in both the rat and human hippocampus.

As noted above, the hippocampus is associated with both schizophrenia, and general memory processes in humans. In rodents, compound 23 produces memory enhancing effects in both the step-down passive avoidance assay as well as in the spatial water maze assay. Without being bound by a particular theory, it is believed that the D4 receptors located in the hippocampus mediate the memory enhancing effects of the compounds of the invention. Therefore, since (1) compound 23 is active in animal models that are predictive of cognition enhancement, and specifically enhancement of memory and learning, and (2) compound 23 binds to D4 receptors in the hippocampus, the D4 class of dopamine antagonists, including the compounds of the invention, are useful for enhancing memory in humans.

Thus, the invention further provides methods for enhancing cognition, and specifically learning and memory, in mammals. These methods comprise administering to a mammal such as a human a compound of the invention in an amount effective to enhance cognition.

DETAILED DESCRIPTION OF THE INVENTION

Figure 1:
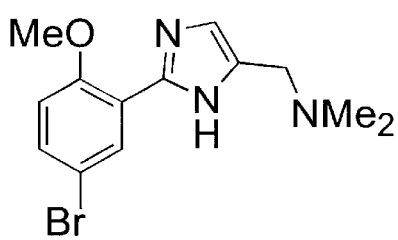
FIGS. 1, 2, and 3 show representative substituted aminomethylimidazoles of the present invention.
Figure 1:
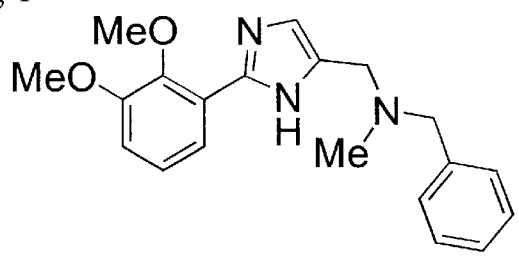
Figure 1:
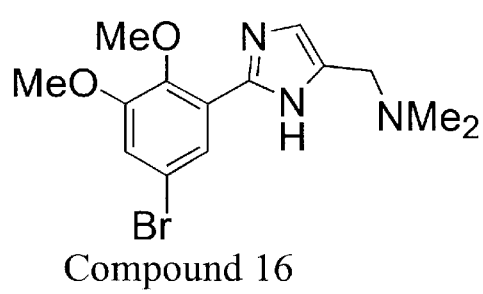
Figure 1:
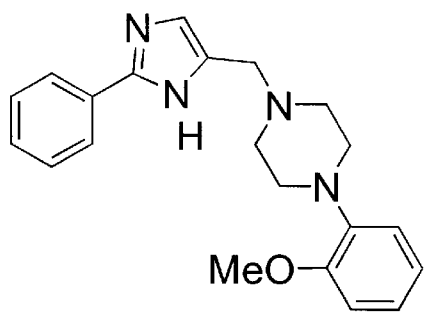
Figure 1:
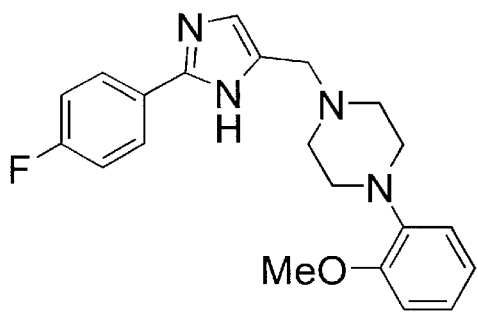
Figure 1:
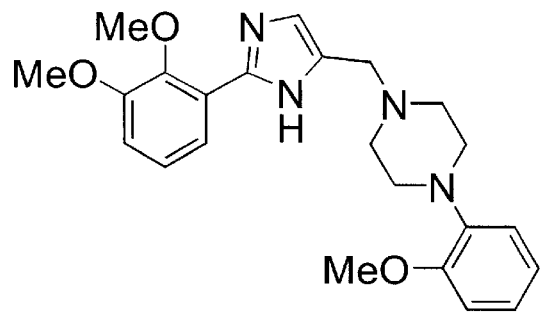
Figure 1:
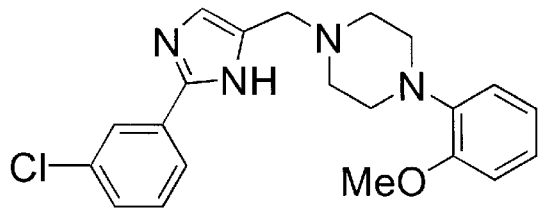
Figure 1:
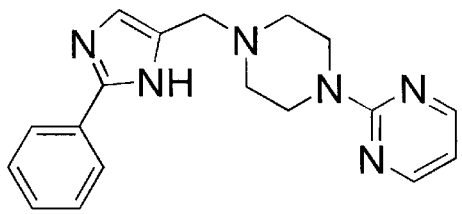
Figure 2:
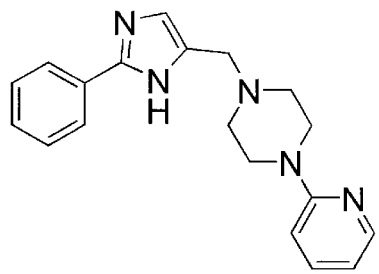
Figure 2:
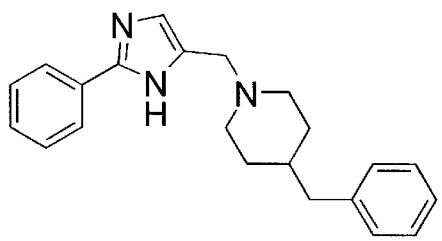
Figure 2:
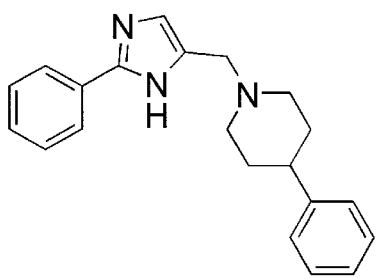
Figure 2:
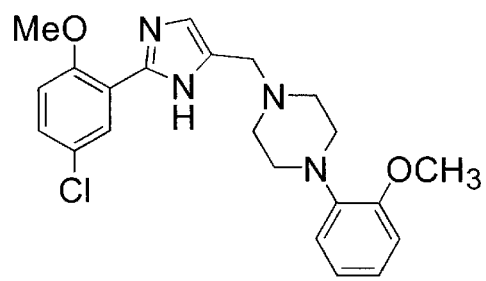
Figure 2:
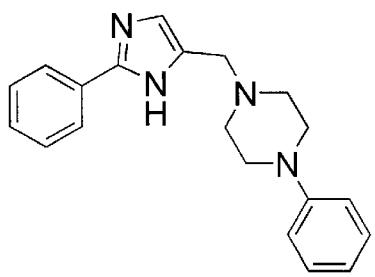
Figure 2:
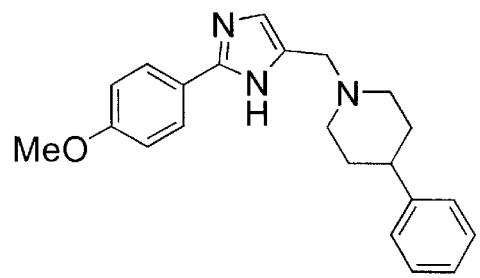
Figure 2:
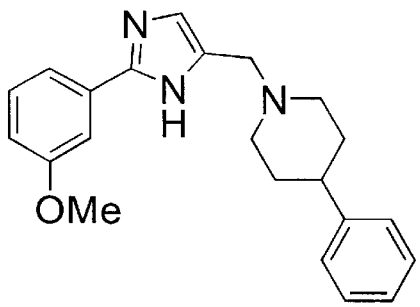
Figure 2:
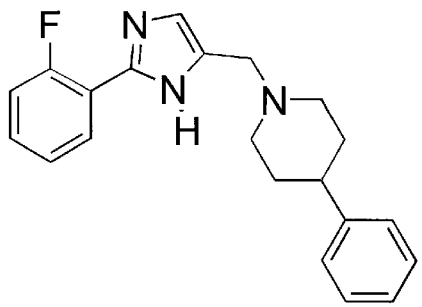
Figure 3:
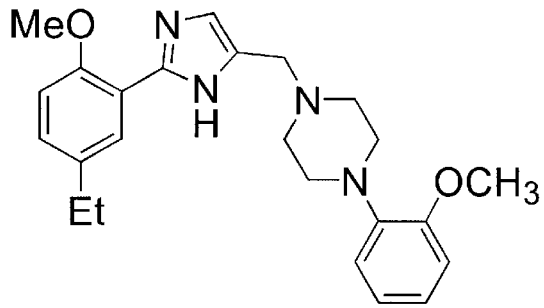
Figure 3:
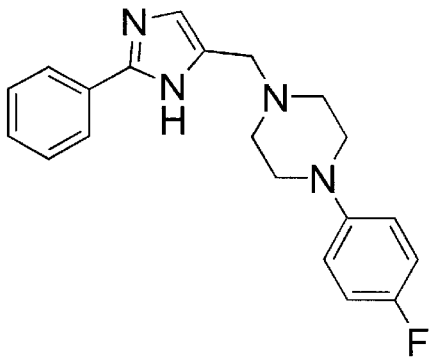
Figure 3:
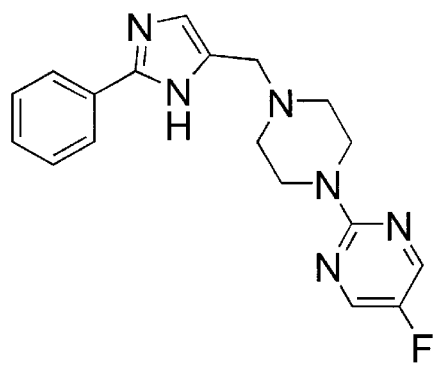
Figure 3:
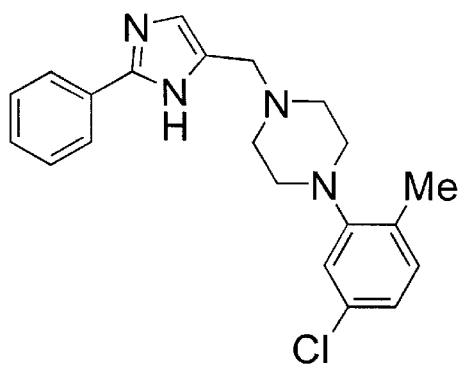
Figure 3:
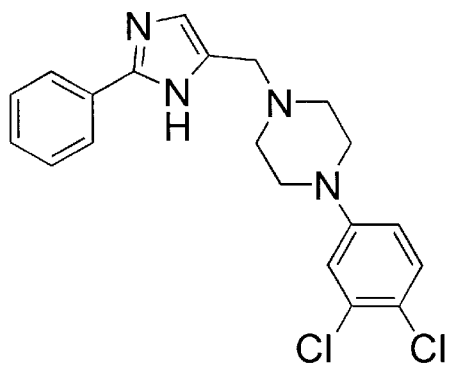
Figure 3:
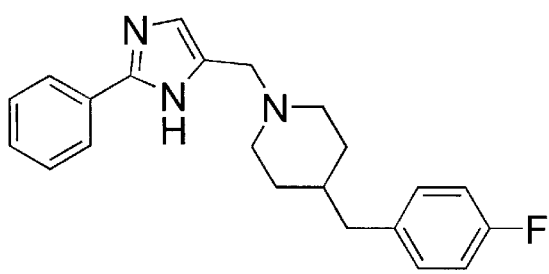

In addition to compounds of general formula I described above, the present invention further encompasses compounds of Formula II:

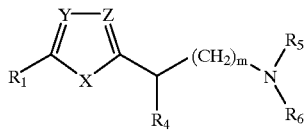

II where
$R_1$, X, Y, Z, m are as defined above for Formula I;
$R_3$ is hydrogen, halogen, straight or branched chain lower alkyl having 1–6 carbon atoms;
$R_4$ is hydrogen or straight or branched chain lower alkyl having 1–6 carbon atoms, or, where Z is $CR_3$, $R_3$ and $R_4$ together may represent —$(CH_2)_{n1}$— where n1 is 2, 3 or 4; or $R_2$ and $R_4$ together may represent —$(CH_2)_{n2}$— where n2 is 2, 3 or 4.
$R_2$ and $R_5$ together may represent —$(CH_2)_{n3}$— where n3 is 2 or 3;
$R_6$ is hydrogen, straight or branched chain lower alkyl, phenyl or arylalkyl; or
$NR_5R_6$ represents:

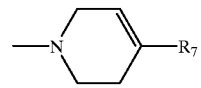

where $R_7$ is as defined for Formula I.
$NR_5R_6$ represents:

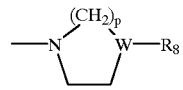

where p, and is 1, 2, or 3;
W is N and $R_8$ is phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or
W is CH and $R_8$ is optionally substituted phenyl or an arylalkyl group such as, for example, phenylalkyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

Preferred compounds according to Formula I include those where Z is $CR_3$ and $R_3$ and $R_4$ together form a 5 or 6-membered ring; $R_1$ is substituted or unsubstituted phenyl; X is: N; Y is: N; and $R_5$ and $R_6$ represents:

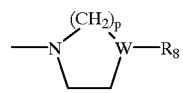

where p is 2; and
W is N and $R_8$ is phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or W is CH and $R_8$ is optionally substituted phenyl or an arylalkyl group such as, for example, phenylalkyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

Preferred compounds according to Formula II are those where $R_1$ is phenyl optionally substituted in the 4-position with halogen or alkyl, Y and X are nitrogen, Z is CH, $R_4$ is hydrogen, m is 0, and $NR_4R_5$ represents 4-substituted piperazin-1-yl or 4-substituted piperidin-1-yl. The piperazinyl or piperidinyl groups are substituted in the 4-position with pyridyl or pyrimidinyl, or phenyl or benzyl each of which is optionally substituted, preferably in the 4-position, with halogen, alkyl, or alkoxy. The preferred piperidinyl groups are optionally substituted in the 3-position with alkyl, and more preferably, methyl, groups. Particularly preferred $R_1$ groups are 4-methylphenyl and 4-halophenyl groups.

The present invention also encompasses compounds of Formula IIA:

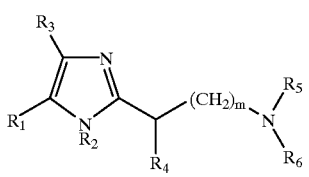

IIA where
- $R_1$ is: aryl, heteroaryl, arylalkyl, cycloalkyl or naphthyl; unsubstituted or substituted by up to 3 substituents which may be the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$;
- $R_2$ is hydrogen or alkyl;
- $R_3$ is: hydrogen, lower alkyl, halogen, hydroxy lower alkyl, or phenyl unsubstituted or substituted by up to three substituents independently selected from hydrogen, halogen, trifluoromethyl, cyano, sulfonamido, hydroxy, straight or branched chain lower alkyl having 1–6 carbon atoms, or straight or branched chain lower alkoxy having 1–6 carbon atoms;
- $R_4$ is: hydrogen or straight or branched chain lower alkyl having 1–6 carbon atoms, or $R_3$ and $R_4$ together may represent —$(CH_2)_{n1}$— where n1 is 2, 3 or 4; or $R_2$ and $R_4$ together may represent —$(CH_2)_{n2}$— where n2 is 2, 3 or 4.
- m is: zero, one or two
- $R_5$ and $R_6$ are the same or different and represent hydrogen, straight or branched chain lower alkyl having 1–6 carbon atoms, aryl, straight or branched chain lower alkyl having 1–6 carbon atoms or $R_2$ and $R_5$ together may represent —$(CH_2)_{n3}$— where n3 is 2 or 3; or
- $NR_5R_6$ together represent: 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or
- $NR_5R_6$ represents:

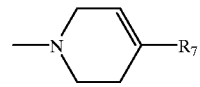

where $R_7$ is phenyl, benzyl or phenethyl with the phenyl ring unsubstituted or substituted with up to three substituents which may be the sane or different and represent hydrogen, halogen, trifluoromethyl, hydroxy, straight or branched chain lower alkyl having 1–6 carbon atoms, or straight or branched chain lower alkoxy having 1–6 carbon atoms; or $NR_5R_6$ represents:

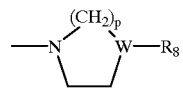

where p is 1, 2, or 3; and
- W is N and $R_8$ is hydrogen, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or
- W is CH and $R_8$ is optionally substituted phenyl, optionally substituted benzoyl, or an arylalkyl group such as, for example, phenylalkyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

Preferred compounds of Formula IIA are those where $R_1$ is optionally substituted phenyl; $R_2$ and $R_4$ are hydrogen; and $R_5$ is alkyl and $R_6$ is arylalkyl, preferably optionally substituted, and more preferably unsubstituted, benzyl; or $NR_5R_6$ is:

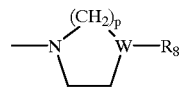

where p, W, and $R_8$ are as defined above for Formula I.

Particularly preferred compounds of Formula IIA are those where $R_1$ is optionally substituted phenyl; $R_2$ and $R_4$ are hydrogen; $R_5$ is alkyl and $R_6$ is arylalkyl, preferably optionally substituted, and more preferably unsubstituted, benzyl; or $NR_5R_6$ is:

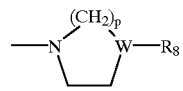

where p, is 2;
W is N and $R_8$ is phenyl, pyridyl or pyrimidinyl, unsubstituted or mono or disubstituted with halogen, or straight or branched chain lower alkoxy having 1–6 carbon atoms.

Particularly preferred compounds of Formula IIA are those where $R_1$ is optionally substituted phenyl; $R_2$ and $R_4$ are hydrogen; $R_3$ is hydrogen; $R_5$ is alkyl and $R_6$ is arylalkyl, preferably optionally substituted, and more preferably unsubstituted, benzyl; or $NR_5NR_6$ is:

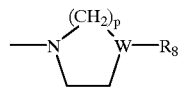

where p, is 2;

W is N and $R_8$ is phenyl, pyridyl or pyrimidinyl, unsubstituted or mono or disubstituted with halogen, or straight or branched chain lower alkoxy having 1–6 carbon atoms.

Other particularly preferred compounds of Formula IIA are those where $R_1$ is phenyl; $R_2$ and $R_4$ are hydrogen; $R_3$ is hydrogen; and $NR_5R_6$ is:

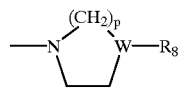

where p, is 2; and

W is CH and $R_8$ is optionally halogenated or alkoxylated phenyl or an arylalkyl group such as, for example, phenylalkyl where the phenyl ring is optionally substituted with up to three substituents independently selected from hydrogen, halogen, or straight or branched chain lower alkoxy having 1–6 carbon atoms.

The present invention also encompasses compounds of Formula III:

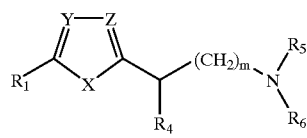

III where $R_1$ is aryl, heteroaryl, or naphthyl; unsubstituted or substituted by up to three substituents which may be the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$;

X, Y, Z, m, are as defined above for Formula I;

$R_3$ is hydrogen, halogen, straight or branched chain lower alkyl having 1–6 carbon atoms;

$R_4$ is hydrogen or straight or branched chain lower alkyl having 1–6 carbon atoms, or, when Z is $CR_3$, $R_3$ and $R_4$ together may represent —$(CH_2)_{n1}$— where n1 is 2, 3 or 4;

$NR_5R_6$ represents:

where $R_7$ is as defined above for Formula I; or $NR_5R_6$ represents:

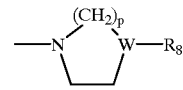

where p, and is 1, 2, or 3;

W is N and $R_8$ is phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or W is CH and $R_8$ is optionally substituted phenyl or an arylalkyl group such as, for example, phenylalkyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

In addition, the present invention encompasses compounds of Formula IV:

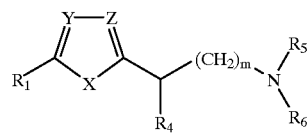

IV where $R_1$ is phenyl or naphthyl, each of which may be substituted by up to three substituents independently selected from hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$.

X, Y, Z, are as defined above for Formula I, $R_3$ is hydrogen, halogen, straight or branched chain lower alkyl having 1–6 carbon atoms;

$R_4$ is hydrogen or straight or branched chain lower alkyl having 1–6 carbon atoms;

m is zero;

$NR_5R_6$ represents:

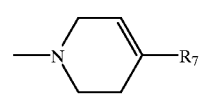

where $R_7$ is as defined above for Formula I; or $NR_5R_6$ represents:

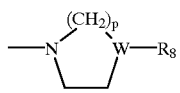

where p, and is 1, 2, or 3;
W is N and $R_8$ is phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or
W is CH and $R_8$ is optionally substituted phenyl or an arylalkyl group such as, for example, phenylalkyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

The invention further encompasses compounds of Formula V:

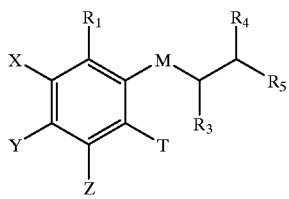

V and the pharmaceutically acceptable non-toxic salts thereof wherein
$R_1$ and T are the same or different and represent hydrogen, halogen, hydroxy, straight or branched chain lower alkyl having 1–6 carbon atoms, or straight or branched chain lower alkoxy having 1–6 carbon atoms;
M is

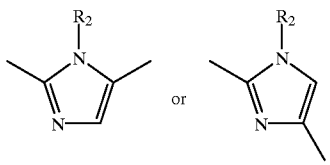

where $R_2$ is hydrogen or straight or branched chain lower alkyl having 1–6 carbon atoms, or $R_1$ and $R_2$ together may represent $-(CH_2)_{n1}$ where n1 is 1, 2, or 3;
X and Z are the same or different and represent hydrogen, halogen, hydroxy, straight or branched chain lower alkyl having 1–6 carbon atoms, straight or branched chain lower alkoxy having 1–6 carbon atoms or $SO_2R_6$ where $R_6$ is straight or branched chain lower alkyl having 1–6 carbon atoms;
Y is hydrogen, halogen, amino, or straight or branched chain lower alkyl having 1–6 carbon atoms;
$R_3$ is hydrogen or straight or branched chain lower alkyl having 1–6 carbon atoms, or $R_3$ and $R_4$ together may represent $-(CH_2)_{n2}-$ where n2 is 3 or 4; and
$R_4$ and $R_5$ are the same or different and represent hydrogen, straight or branched chain lower alkyl having 1–6 carbon atoms, or phenylalkyl or pyridylalkyl where each alkyl is straight or branched chain alkyl having 1–6 carbon atoms; or
$R_2$ and $R_5$ together may represent $-(CH_2)_{n3}-$ where n3 is 2 or 3; or
$NR_4R_5$ represents 2-(1,2,3,4-tetrahydroisoquinolinyl), or 2-(1,2,3,4-tetrahydroiso-quinolinyl) mono or disubstituted with halogen, hydroxy, straight or branched chain lower alkyl having 1–6 carbon atoms, or straight or branched chain lower alkoxy having 1–6 carbon atoms; or

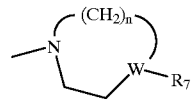

where W is N or CH; and
$R_7$ is hydrogen, phenyl, pyridyl or pyrimidinyl, or phenyl, pyridyl or pyrimidinyl, each of which is mono or disubstituted with halogen, hydroxy, straight or branched chain lower alkyl having 1–6 carbon atoms, or straight or branched chain lower alkoxy having 1–6 carbon atoms; or
W—$R_7$ is oxygen or sulfur, and
n is 1, 2, or 3.

The present invention further encompasses compounds of Formula VI:

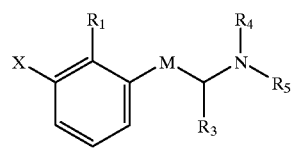

VI wherein
$R_1$ is hydrogen, halogen, hydroxy, straight or branched chain lower alkyl having 1–6 carbon atoms, or straight or branched chain lower alkoxy having 1–6 carbon atoms;
M is

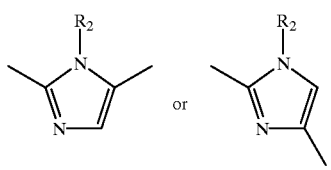

where $R_2$ is hydrogen or, straight or branched chain lower alkyl having 1–6 carbon atoms, or $R_1$ and $R_2$ together may represent $-(CH_2)_{n1}$ where n1 is 1, 2, or 3;
X is hydrogen, halogen, hydroxy, straight or branched chain lower alkyl having 1–6 carbon atoms, straight or branched chain lower alkoxy having 1–6 carbon atoms or $SO_2R_6$ where $R_6$ is straight or branched chain lower alkyl having 1–6 carbon atoms;
$R_3$ is hydrogen or straight or branched chain lower alkyl having 1–6 carbon atoms, or $R_3$ and $R_4$ together may represent $-(CH_2)_{n2}-$ where n2 is 3 or 4; and
$R_4$ and $R_5$ are the same or different and represent hydrogen, straight or branched chain lower alkyl having 1–6 carbon atoms, phenylalkyl or pyridylalkyl where each alkyl is straight or branched chain lower alkyl having 1–6 carbon atoms; or $R_2$ and $R_5$ together may represent —$(CH_2)_{n3}$— where n3 is 2 or 3; or $R_5$ represents 2-(1,2,3,4tetrahydroisoquinolinyl) or 2-(1,2,3,4tetrahydroiso-quinolinyl) mono or disubstituted with halogen, hydroxy, straight or branched chain lower alkyl having 1–6 carbon atoms, or straight or branched chain lower alkoxy having 1–6 carbon atoms; or

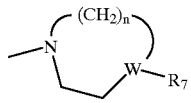

where
W is N or CH;
$R_7$ is hydrogen, phenyl, pyridyl or pyrimidinyl, or
phenyl, pyridyl or pyrimidinyl, each of which may be mono or disubstituted with halogen, hydroxy, straight or branched chain lower alkyl having 1–6 carbon atoms, or straight or branched chain lower alkoxy having 1–6 carbon atoms; or
W—$R_7$ is oxygen or sulfur; and
n is 1, 2, or 3.

The present invention also encompasses compounds of Formula VII:

VII

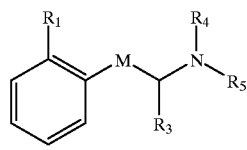

wherein
$R_1$ is hydrogen, halogen, hydroxy, straight or branched chain lower alkyl having 1–6 carbon atoms, or straight or branched chain lower alkoxy having 1–6 carbon atoms;
M is

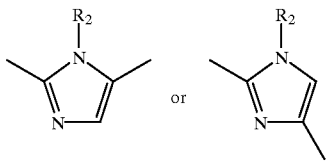

where $R_2$ is hydrogen, or straight or branched chain lower alkyl having 1–6 carbon atoms, or $R_1$ and $R_2$ together may represent —$(CH_2)_{n1}$ where n1 is 1, 2, or 3;
$R_3$ is hydrogen, or straight or branched chain lower alkyl having 1–6 carbon atoms, or $R_3$ and $R_4$ together may represent —$(CH_2)_{n2}$— where n2 is 3 or 4; or
$R_4$ and $R_5$ are the same or different and represent hydrogen, straight or branched chain lower alkyl having 1–6 carbon atoms, aryl straight or branched chain lower alkyl having 1–6 carbon atoms or $R_2$ and $R_5$ together may represent —$(CH_2)_{n3}$— where n3 is 2 or 3; or $NR_4R_5$ represents 2-(1,2,3,4-tetrahydroisoquinolinyl), or 2-(1,2,3,4-tetrahydroiso-quinolinyl) mono or disubstituted with halogen, hydroxy, straight or branched chain lower alkyl having 1–6 carbon atoms, or straight or branched chain lower alkoxy having 1–6 carbon atoms; or

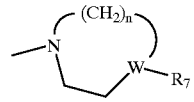

where
W is N or CH;
$R_7$ is
hydrogen, phenyl, pyridyl or pyrimidinyl; or
phenyl, pyridyl or pyrimidinyl mono or disubstituted with halogen, hydroxy, straight or branched chain lower alkyl having 1–6 carbon atoms, or straight or branched chain lower alkoxy having 1–6 carbon atoms; or
W—$R_7$ is oxygen or sulfur; and
n is 1, 2, or 3.

In addition, the present invention encompasses compounds of Formula VIII:

VIII

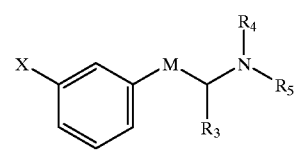

wherein
M is

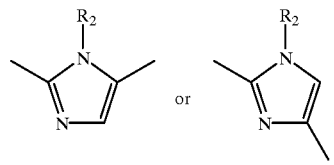

where $R_2$ is hydrogen or, straight or branched chain lower alkyl having 1–6 carbon atoms, or $R_1$ and $R_2$ together may represent —$(CH_2)_{n1}$ where n1 is 1, 2, or 3;
X is hydrogen, halogen, hydroxy, straight or branched chain lower alkyl having 1–6 carbon atoms, straight or branched chain lower alkoxy having 1–6 carbon atoms, or $SO_2R_6$ where $R_6$ is straight or branched chain lower alkyl having 1–6 carbon atoms;
$R_3$ is hydrogen, or straight or branched chain lower alkyl having 1–6 carbon atoms, or $R_3$ and $R_4$ together may represent —$(CH_2)_{n2}$— where n2 is 3 or 4; and
$R_4$ and $R_5$ are the same or different and represent hydrogen, straight or branched chain lower alkyl having 1–6 carbon atoms, phenylalkyl or pyridylalkyl where each alkyl is straight or branched chain lower alkyl having 1–6 carbon atoms; or
$R_2$ and $R_5$ together may represent —$(CH_2)_{n3}$— where n3 is 2 or 3; or
$NR_4R_5$ represents 2-(1,2,3,4-tetrahydroisoquinolinyl), or 2-(1,2,3,4-tetrahydroiso-quinolinyl) mono or disubstituted with halogen, hydroxy, straight or branched chain lower alkyl having 1–6 carbon atoms, or straight or branched chain lower alkoxy having 1–6 carbon atoms; or

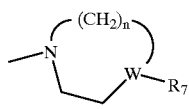

where W is N or CH;
R$_7$ is hydrogen, phenyl, pyridyl or pyrimidinyl, or hydrogen, phenyl, pyridyl or pyrimidinyl, mono or disubstituted with halogen, hydroxy, straight or branched chain lower alkyl having 1–6 carbon atoms, or straight or branched chain lower alkoxy having 1–6 carbon atoms; or
W—R$_7$ is oxygen or sulfur, and
n is 1, 2, or 3.

The invention also provides compounds of Formula IX:

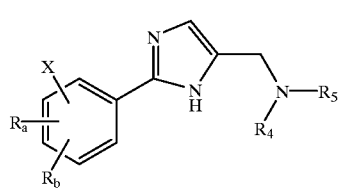

where
X represents a hydrogen or halogen;
R$_a$ and R$_b$ are the same or different and represent hydrogen or alkoxy; and
NR$_4$R$_5$ represents 4-(substituted or unsubstituted phenyl) piperazin-1-yl or 4-phenyl-piperidin-1-yl, where the phenyl group may be substituted with hydrogen, alkyl, or alkoxy.

The invention also provides compounds of Formula X:

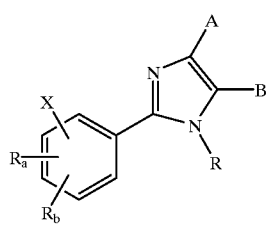

where
X represents a hydrogen or halogen;
R represents hydrogen or alkyl;
R$_a$ and R$_b$ are the same or different and represent hydrogen or alkoxy; and
A and B are the same or different and represent hydrogen or (4-(2-pyrimidinyl)piperazin-1-yl)methyl.

Preferred compounds of Formula X are those where R is hydrogen or methyl and X, R$_a$ and R$_b$ are hydrogen. Particularly preferred compounds of Formula X are those where R is hydrogen or methyl, X, R$_a$ and R$_b$ are hydrogen, and A and B are different and represent hydrogen or (4-(2-pyrimidinyl)piperazin-1-yl)methyl.

Also within the scope of the invention are compounds of Formula XI:

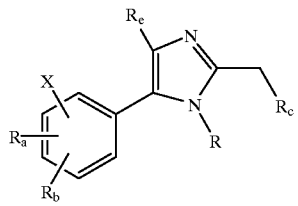

where
X represents a hydrogen or halogen;
R represents hydrogen or alkyl;
R$_a$ and R$_b$ are the same or different and represent hydrogen or alkoxy; and
R$_c$ is a group of the formula:

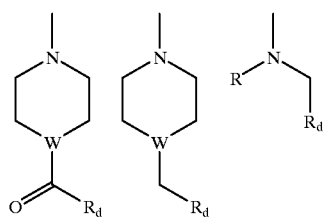

where
W is N or CH;
R represents alkyl;
R$_d$ represents pyridyl, pyrimidinyl, phenylalkyl, or phenyl optionally substituted with halogen, alkyl or alkoxy; and
R$_e$ is alkyl.

Preferred compounds of Formula XI are those where X, R$_a$, R$_b$, and R$_e$ are hydrogen and R$_c$ is a 4-substituted piperazin-1-yl or piperidin-1-yl group. Particularly preferred compounds of Formula XI are those where the 4-substituted piperazin-1-yl or piperidin-1-yl groups are substituted with optionally substituted phenyl, phenylalkyl, 2-pyridyl or 2-pyrimidinyl groups. Other preferred compounds of formula XI are those where X, R$_a$, R$_b$, and R$_e$ are hydrogen, R$_e$ is methyl and R$_c$ is piperazin-1-yl or piperidin-1-yl each of which is substituted in the 4-position with benzyl, pyridyl or pyrimidinyl.

The invention also provides compounds of Formula XII:

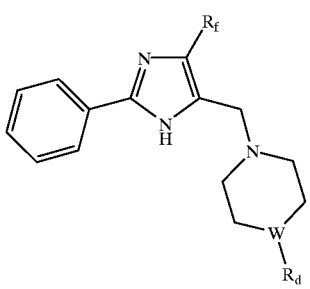

where
W is N or CH;
R$_f$ is halogen or alkyl;
R$_d$ is pyridyl, pyrimidinyl, phenylalkyl, or phenyl optionally substituted with halogen, alkyl or alkoxy.

Preferred compounds of Formula XII are those where $R_f$ is halogen or methyl, W is nitrogen, and $R_d$ is pyridyl, pyrimidinyl, or benzyl. Particularly preferred compounds of Formula XII are those where $R_f$ is halogen or methyl, W is nitrogen, and $R_d$ is pyrimidinyl.

The invention further provides compounds of Formula XIII:

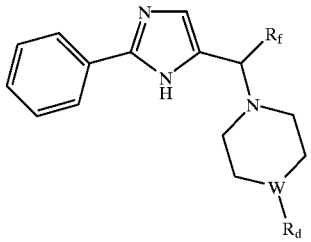

XIII where

W is N or CH;

$R_f$ is alkyl; and $R_d$ is pyridyl, pyrimidinyl, phenylalkyl, or phenyl optionally substituted with halogen, alkyl or alkoxy.

Preferred compounds of Formula XIII are those where $R_f$ is methyl, W is nitrogen, and $R_d$ is pyridyl, pyrimidinyl, or benzyl. Particularly preferred compounds of Formula XIII are those where $R_f$ is methyl, W is nitrogen, and $R_d$ is pyrimidinyl.

The invention further provides compounds of Formula XIV:

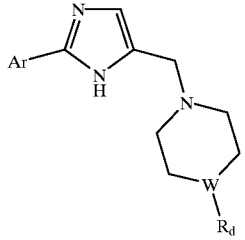

XIV where

Ar is 1- or 2-naphthyl, 2-, 3-, or 4-pyridyl, 2-pyrazinyl, 2-thienyl, or 2-quinolinyl, W is N or CH;

$R_d$ is pyridyl, pyrimidinyl, phenylalkyl, or phenyl optionally substituted with halogen, alkyl or alkoxy.

Preferred compounds of Formula XIV are those where W is CH, and $R_d$ is pyridyl, pyrimidinyl, or benzyl.

The invention further provides compounds of Formula XV:

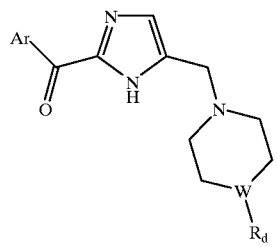

XV where

Ar is 1- or 2-naphthyl, phenyl or phenyl mono-, di- or trisubstituted with alkyl, alkoxy or halogen, W is N or CH;

$R_d$ is pyridyl, pyrimidinyl, phenylalkyl, or phenyl optionally substituted with halogen, alkyl or alkoxy.

Preferred compounds of Formula XV are those where Ar is phenyl, W is CH, and $R_d$ is pyridyl, pyrimidinyl, or benzyl.

The invention further provides compounds of Formula XVI:

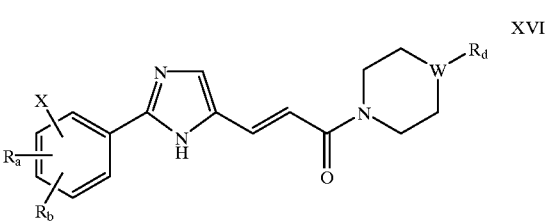

XVI where

X represents a hydrogen or halogen;

$R_a$ and $R_b$ are the same or different and represent hydrogen or alkoxy;

W is N or CH, $R_d$ is pyridyl, pyrimidinyl, phenylalkyl, or phenyl optionally substituted with halogen, hydroxy, alkyl or alkoxy.

Preferred compounds of Formula XVI are those where X, $R_a$ and $R_b$ are hydrogen, W is CH, and $R_d$ is pyridyl, pyrimidinyl, or benzyl.

The invention further provides compounds of Formula XVII:

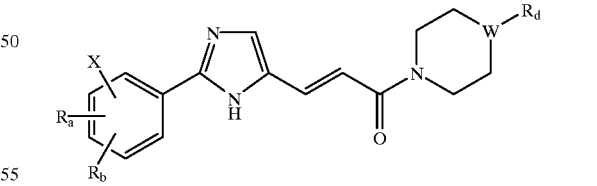

XVII where

X represents a hydrogen or halogen;

$R_a$ and $R_b$ are the same or different and represent hydrogen or alkoxy;

W is N or CH;

$R_d$ is pyridyl, pyrimidinyl, phenylalkyl, or phenyl optionally substituted with halogen, hydroxy, alkyl or alkoxy.

Preferred compounds of Formula XVII are those where X, $R_a$ and $R_b$ are hydrogen, W is N, and $R_d$ is pyridyl, pyrimidinyl, or benzyl.

The invention further provides compounds of Formula XVIII:

XVIII where m is 0, 1 or 2;

X represents a hydrogen or halogen, $R_a$ and $R_b$ are the same or different and represent hydrogen or alkoxy;

W is N or CH;

$R_d$ is pyridyl, pyrimidinyl, phenylalkyl, or phenyl optionally substituted with halogen, hydroxy, alkyl or alkoxy.

Preferred compounds of Formula XVIII are those where X, $R_a$ and $R_b$ are hydrogen, W is N, and $R_d$ is pyridyl, pyrimidinyl, or benzyl.

The invention further provides compounds of Formula XIX:

XIX where m is 0, 1 or 2;

X represents a hydrogen or halogen;

$R_a$ and $R_b$ are the same or different and represent hydrogen or alkoxy;

W is N or CH;

$R_d$ is pyridyl, pyrimidinyl, phenylalkyl, or phenyl optionally substituted with halogen, hydroxy, alkyl or alkoxy.

Preferred compounds of Formula XIX are those where X, $R_a$ and $R_b$ are hydrogen, W is N, and $R_d$ is pyridyl, pyrimidinyl, or benzyl. Other preferred compounds of formula XIX are those where X, $R_a$ and $R_b$ are hydrogen, W is CH, and $R_d$ is phenyl substituted with halogen and/or hydroxy.

The invention also provides compounds of Formula XX:

XX where $R_a$ is alkyl;

W is N or CH;

$R_d$ is pyridyl, pyrimidinyl, phenylalkyl, or phenyl optionally substituted with halogen, alkyl or alkoxy.

Preferred compounds of Formula XX are those where W is nitrogen, $R_a$ is hydrogen or methyl, and $R_d$ is pyridyl, pyrimidinyl, or benzyl. Other preferred compounds according to Formula XX are those where W is CH, $R_a$ is hydrogen or methyl, and $R_d$ is pyridyl, pyrimidinyl, or benzyl.

The invention also provides compounds of Formula XXI:

XXI where

W is N or CH and $R_d$ is pyridyl, pyrimidinyl, phenylalkyl, or phenyl optionally substituted with halogen, alkyl or alkoxy.

Preferred compounds of Formula XXI are those where W is nitrogen, $R_a$ is hydrogen or methyl, and $R_d$ is pyridyl, pyrimidinyl, or benzyl. Other preferred compounds according to Formula XXI are those where W is CH, $R_a$ is hydrogen or methyl, and $R_d$ is pyridyl, pyrimidinyl, or benzyl.

Representative compounds of the present invention, which are encompassed by Formula I, include, but are not limited to the compounds in FIG. 1 and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of nontoxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

By "lower alkoxy" and "alkoxy" is meant straight and branched chain alkoxy groups having from 1–6 carbon atoms.

By "hydroxy lower alkyl" or "hydroxy alkyl" is meant an alkyl group substituted by at least one hydroxy group. Preferred hydroxy alkyl groups are straight chain alkyl groups substituted with one hydroxy group at the terminal carbon atom.

By "heteroaryl" is meant 5, 6, or 7 membered aromatic ring systems having at least one hetero atom selected from the group consisting of nitrogen, oxygen and sulfur. Examples of heteroaryl groups are pyridyl, pyrimidinyl, pyrrolo, pyrazolo, pyrazinyl, pyridazinyl, oxazolo, furanyl, quinoline, isoquinoline, thiazole, and thienyl, which can optionally be unsubstituted or substituted with e.g., halogen, lower alkyl, lower alkoxy, lower alkylthio, trifluoromethyl, lower acyloxy, aryl, heteroaryl, and hydroxy.

By "halogen" is meant fluorine, chlorine, bromine and iodine.

By "arylalkyl" is meant the group -R-Ar where Ar is an aryl group and R is a straight or branched chain aliphatic group. Arylalkyl groups may optionally be substituted with, e.g., halogen, lower alkyl, lower alkoxy, lower alkylthio, trifluoromethyl, lower acyloxy, and hydroxy. Preferred arylalkyl groups in the above formulas where W is CH and $R_8$ represents arylalkyl are phenylalkyl groups where the alkyl portion is lower alkyl. A particularly preferred phenylalkyl group is benzyl where the phenyl ring may be substituted with up to the substituents independently selected from hydrogen, halogen, trifluoromethyl, hydroxy, straight or branched chain lower alkyl having 1–6 carbon atoms, or straight or branched chain lower alkoxy having 1–6 carbon atoms.

By "cycloalkyl" is meant cyclic hydrocarbons having from 3–8 carbon atoms. These cyclic hydrocarbon groups may be substituted with up to three substituents independently selected from hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$.

The pharmaceutical utility of compounds of this invention are indicated by the following assays for dopamine receptor subtype affinity.

Assay for D2 and D3 Receptor Binding Activity

Striatal tissue is dissected from adult male Sprague Dawley rats or BHK 293 cells are harvested containing recombinantly produced D2 or D3 receptors. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubators are carried out at 48° C. and contain 0.5 ml of tissue sample, 0.5 nM $^3$H-raclopride and the compound of interest in a total incubation volume of 1.0 ml. Nonspecific binding is defined as that binding found in the presence of $10^{-4}$ M dopamine; without further additions, nonspecific binding is less than 20% of total binding. The binding characteristics of examples of this patent are shown in Table 1 for rat striatal homogenates.

TABLE I

| Compound Number[1] | IC$_{50}$ (mM) |
|---|---|
| 1 | 0.900 |
| 8 | 0.011 |
| 16 | 0.014 |
| 19 | 0.100 |
| 21 | 0.018 |
| 24 | 0.620 |
| 26 | 0.200 |

[1]Compound numbers relate to compounds described in the examples below and/or shown in the figures.

Assay for D4 Receptor Binding Activity

Clonal cell lines expressing the human dopamine D4 receptor subtype were harvested in PBS and the cells centrifuged and the pellets stored at −80° C. until used in the binding assay. The pellets were resuspended and the cells lysed at 4° C. in 50 mM Tris pH 7.4 buffer containing 120 mM NaCl, 1 mM EDTA and 5 mM MgCl$_2$. The homogenate is centrifuged at 48000×g for 10 minutes at 4° C. The resulting pellet is resuspended in fresh buffer and centrifuged again. After resuspension of the pellet in fresh buffer at 100 ml aliquot is removed for protein determination. The remaining homogenate is centrifuged as above, the supernatant removed and the pellet stored at 4° C. until needed at which time it is resuspended to a final concentration of 625 mg/ml (250 mg per sample) with 50 mM Tris buffer (pH 7.4) and 120 mM NaCl just prior to use. Incubations were carried out for 60 minutes at 25° C. in the presence of 0.1 nM [$^3$H] YM-09151-2. The incubation was terminated by rapid filtration through Whatman GF/C filters and rinsed with 2×4 ml washes of chilled 50 mM Tris (pH 7.4) and 120 mM NaCl. Non-specific binding was determined with 1 mM spiperone and radioactivity determined by counting in an LKB beta counter. Binding parameters were determined by non-linear least squares regression analysis, from which the inhibition constant (Ki) could be calculated for each test compound The binding characteristics of some examples of this patent are shown in Table 2 for the dopamine D4 binding assay. In general, compounds of the accompanying examples were tested in the above assay, and all were found to possess a Ki value for the displacement of [$^3$H]YM-09151-2 from the human dopamine D4 receptor subtype of below 500 nM. Some specific data is indicated in Table 2.

TABLE 2

| Compound Number[1] | Ki (mM) |
|---|---|
| 19 | 0.001 |
| 20 | 0.014 |
| 22 | 0.048 |
| 23 | 0.003 |
| 24 | 0.001 |
| 25 | 0.002 |
| 43 | 0.014 |
| 45 | 0.005 |
| 47 | 0.053 |
| 50 | 0.005 |
| 52 | 0.002 |
| 55 | 0.500 |
| 56 | 0.450 |
| 58 | 0.003 |
| 60 | 0.015 |
| 61 | 0.013 |
| 65 | 0.013 |

[1]Compound numbers relate to compounds described in the examples below and/or shown in the figures.

Compounds 8, 16, 19, 21, 23, 24, 25 and 52 are particularly preferred embodiments of the present invention because of their potency in binding to dopamine receptor subtypes.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of representative 2-phenyl-4-aminomethyl-imidazoles of the present invention is shown in Scheme I. Those having skill in the art will recognize that the starting materials may be varied and additional steps employed to produce compounds encompassed by the present invention.

straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$;

R5 and R6 are as defined as above for Formula I; or $NR_5R_6$ together represent cyclic groups as defined above for Formula I.

Alternatively, compounds of the invention may be prepared according to the reactions shown in Scheme 2.

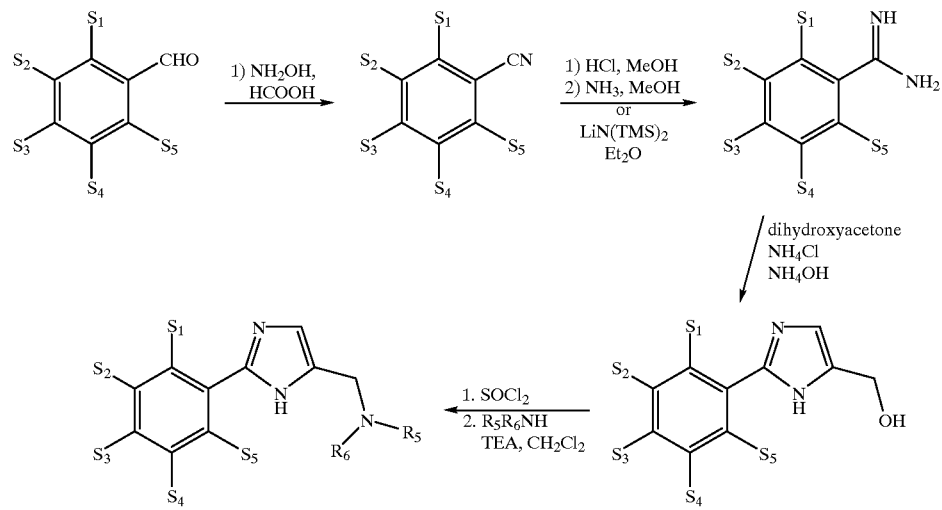

Scheme 1 where $S_1$, $S_2$, $S_3$, $S_4$, and $S_5$ are the same or different and represent hydrogen, halogen, trifluoromethyl, cyano,

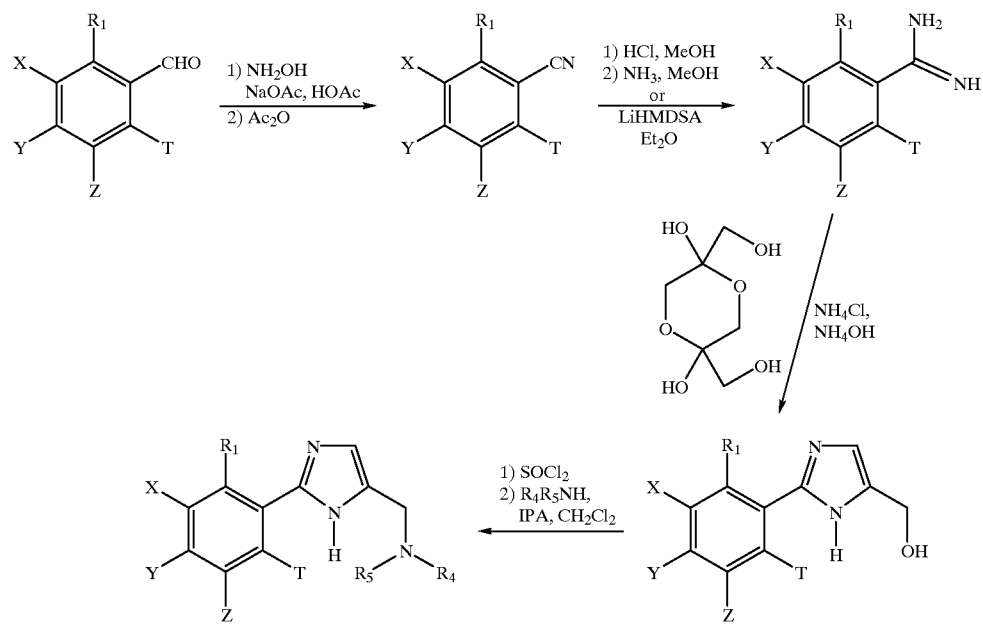

Scheme 2 where $R_1$, T, M, X, Y, Z, $R_4$, and $R_5$ are as defined for Formula V above.

The invention is illustrated further by the following examples which are not to be construed as limiting the invention in scope or spirit to the specific procedures and compounds described in them.

EXAMPLE I

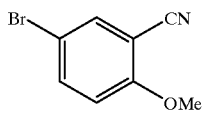

A mixture of 6.45 g 5-bromo-o-anisaldehyde, 2.2 g of hydroxylamine hydrochloride, 4.1 g of sodium formate and 20 mL formic acid were heated at 100° C. with stirring for 1 h. The reaction mixture was poured onto ice water and the mixture was made basic by the careful addition of 50% sodium hydroxide. The product was extracted with ether, the ether extracts were dried over magnesium sulfate and the solvent was removed in vacuo. The residue was crystallized from ether/hexane to afford 5-bromo-2-methoxybenzonitrile.

EXAMPLE II

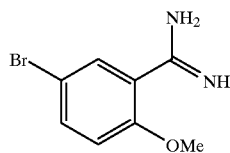

A mixture of 4.0 g 5-bromo-2-methoxybenzonitrile, 5 g 3A molecular sieves and 60 mL of anhydrous methanol was saturated with HCl gas at 0° C. and allowed to stand at 0° C. for 24 h. The solvent was removed in vacuo and the residue taken up in 75 mL of anhydrous methanol and saturated with ammonia gas at room temperature. The reaction mixture was then heated at 80° C. for 4 h in a sealed tube. The solvent was removed in vacuo, the reaction mixture was diluted with 3N HCl and washed with ethyl acetate to remove unreacted nitrile. The aqueous layer was made basic with 50% NaOH and the product was extracted three times with 10% methanol in methylene chloride. The combined organic extracts were dried over potassium carbonate and the solvents removed in vacuo to afford 5-bromo-2-methoxybenzamidine as a glassy solid.

EXAMPLE III

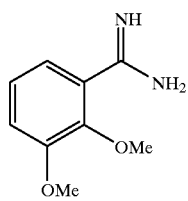

To a solution of 20 g 1,1,1,3,3,3-hexamethyldisilazane in 150 mL dry ether was added 5 mL 2.4 M n-butyllithium in hexane. After 10 min at room temperature,16.3 g 2,3-dimethoxybenzonitrile was added in one portion and the mixture was kept at room temperature for 16 h. The reaction mixture was then poured onto excess 3N HCl. The aqueous layer was separated, basified with 50% NaOH and the product was extracted three times with 10% methanol in methylene chloride. The combined organic extracts were dried over potassium carbonate and the solvents removed in vacuo to afford 2,3-dimethoxybenzamidine as a glassy solid.

EXAMPLE IV

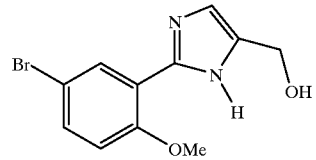

A mixture of 1.5 g of 5-bromo-2-methoxybenzamidine, 1.0 g of 1,3-dihydroxyacetone dimer, 1.3 g of ammonium chloride, 3 mL of tetrahydrofuran and 10 mL concentrated aqueous ammonium hydroxide was heated at 90° C. for 3 h. The reaction mixture was chilled on ice and the precipitated product was collected and recrystallized from methanol to afford 2-(5-bromo-2-methoxyphenyl)-4-hydroxymethylimidazole as a yellow solid.

EXAMPLE V (Compound 1)

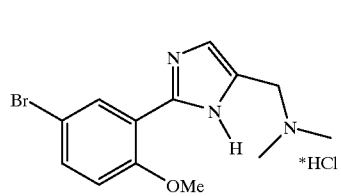

A mixture of 500 mg 2-(5-bromo-2-methoxyphenyl)-4-hydroxymethylimidazole and 1.5 mL thionyl chloride was heated at 80° C. for 15 min and then concentrated under reduced pressure. Diethyl ether (15 mL) was added and the resulting solid was collected and washed with ether. This solid was added in one portion to a mixture of 3 mL of dimethylamine, 15 mL isopropanol and 30 mL of methylene chloride and the mixture was stirred for 20 min. The solvents were removed in vacuo and the residue was dissolved in 2N HCl and washed two times with ethyl acetate. The aqueous layer was made basic with 50% NaOH and the product was extracted with methylene chloride. The organic extracts were dried over magnesium sulfate, the solvents removed in vacuo, and the residue was treated with ethanolic HCl/ether to afford 2-(5-bromo-2-methoxyphenyl)-4(5)-[(N,N-dimethyl)aminomethyl]-imidazole dihydrochloride (Compound 1), m.p. 242–243° C.

EXAMPLE VI

The following compounds were prepared essentially according to the procedure described in Examples I–V:
(a) 2-Phenyl-4(5)-[(N,N-dimethyl)aminomethyl]-imidazole dihydrochloride (Compound 2), m.p. 259–260° C.
(b) 2-Phenyl-4(5)-(piperidinomethyl)-imidazole dihydrochloride (Compound 3), m.p. 245–247° C.
(c) 2-Phenyl-4(5)-[(N-methyl-N-benzyl)aminomethyl]-imidazole dihydrochloride (Compound 4), m.p. 239–240° C.
(d) 2-(2-Methoxyphenyl)-4(5)-[(N,N-dimethyl)aminomethyl]-imidazole dihydrochloride (Compound 5), melting at X° C.

(e) 2-(3-Methoxyphenyl)-4(5)-[(N-methyl-N-benzyl) aminomethyl]-imidazole dihydrochloride (Compound 6), m.p. 115–117° C.

(f) 2-(2,3-Dimethoxyphenyl)-4(5)-[(N,N-dimethyl) aminomethyl]-imidazole dihydrochloride (Compound 7), m.p. 220–221° C.

(g) 2(2,3-Dimethoxyphenyl)-4(5)-[(N-methyl-N-benzyl) aminomethyl]-imidazole dihydrochloride (Compound 8), m.p. 200–202° C.

(h) 2-(3-Methoxyphenyl)-4(5)-[(N,N-diethyl) aminomethyl]-imidazole dihydrochloride (Compound 9), m.p. 213–214° C.

(i) 2-(3-Fluorophenyl)-4(5)-[(N,N-dimethyl) aminomethyl]-imidazole dihydrochloride (Compound 10), m.p. 211–214° C.

(j) 2-(2-Fluorophenyl)-4(5)-[(N-methyl-N-benzyl) aminomethyl]-imidazole dihydrochloride (Compound 11), m.p. 241–244° C.

(k) 2-(3-Methylphenyl)-4(5)-[(N,N-dimethyl) aminomethyl]-imidazole dihydrochloride (Compound 12), m.p. 231–234° C.

(l) 2-(2-Fluorophenyl)-4(5)-[(N,N-dimethyl) aminomethyl]-imidazole dihydrochloride (Compound 13), m.p. 246–247° C.

(m) 2-(4-Fluorophenyl)-4(5)-[(N-methyl-N-benzyl) aminomethyl]-imidazole dihydrochloride (Compound 14), m.p. 237–239° C.

(n) 2-(2-Methoxyphenyl)-4(5)-[(N-methyl-N-benzyl) aminomethyl]-imidazole dihydrochloride (Compound 15), m.p. 239–241° C.

(o) 2-(5-Bromo-2,3-dimethoxyphenyl)-4(5)-[(N,N-dimethyl)aminomethyl]-imidazole dihydrochloride (Compound 16), m.p. 194–194° C.

(p) 2-(5-Bromo-2-methoxyphenyl)-4(5)-[(N-methyl-N-benzyl)aminomethyl]-imidazole dihydrochloride (Compound 17), m.p. 242–243° C.

(q) 2-(5-Bromo-2,3-dimethoxyphenyl)-4(5)-[(N-methyl-N-benzyl)ammomethyl]-imidazole dihydrochloride (Compound 18).

EXAMPLE VII

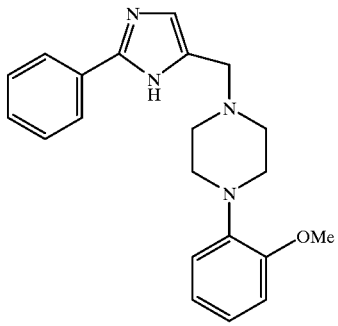

(Compound 19)

A mixture of 350 mg 2-phenyl-4-hydroxymethylimidazole and 3 mL thionyl chloride was heated at 80° C. for 15 min. The excess thionyl chloride was removed in vacuo and the residue was dissolved in 20 mL of methylene chloride. This solution was added to a mixture of 1 mL triethylamine and 410 mg 1-(2-methoxyphenyl) piperazine in 20 mL methylene chloride and the mixture was stirred for 20 min. The solvents were removed in vacuo and the residue was dissolved in 2N HCl and washed two times with ethyl acetate. The aqueous layer was made basic with 50% NaOH and the product was extracted with methylene chloride. The organic extracts were dried over magnesium sulfate, the solvents removed in vacuo, and the residue was crystallized from ethyl acetate to afford 2-phenyl-4(5)-[(4-(2-methoxyphenyl)-piperazin-1-yl)-methyl]imidazole (Compound 19), m.p. 105–107° C.

EXAMPLE VIII

The following compounds were prepared essentially according to the procedure described in Example VII:

(a) 2-(4-Fluorophenyl)-4(5)-[(4-(2-methoxyphenyl)-piperazin-1-yl)-methyl]-imidazole (Compound 20), m.p. 95–97° C.

(b) 2-(2,3-Dimethoxyphenyl)-4(5)-[(4-(2-methoxphenyl)-piperazin-1-yl)-methyl]-imidazole dihydrochloride (Compound 21), m.p. 217–218° C.

(c) 2-(3-Chlorophenyl)-4(5)-[(4-(2-methoxyphenyl)-piperazin-1-yl)-methyl]-imidazole dihydrochloride (Compound 22), m.p. 198–199° C.

(d) 2-Phenyl-4(5)-[(4-(2-pyrimidinyl)-piperazin-1-yl)-methyl]-imidazole dihydrochloride (compound 23), m.p. 246–248° C.

(d') 2-Phenyl-4(5)-[(4-(2-pyrimidinyl)-piperazin-1-yl)-methyl]-imidazole dimaleate (compound 23A), m.p. 176–178° C.

(e) 2-Phenyl-4(5)-[(4-(2-pyridyl)-piperazin-1-yl)-methyl]-imidazole dihydrochloride (Compound 24), m.p. 176–177° C.

(f) 2-Phenyl-4(5)-[(4-benzyl-piperidin-1-yl)-methyl]-imidazole dihydrochloride (Compound 25), m.p. 234–236° C.

(g) 2-Phenyl-4(5)-[(4-phenyl-piperidin-1-yl)-methyl]-imidazole dihydrochloride (Compound 26), m.p. 238–240° C.

(h) 2-Phenyl-4(5)-[(1,2,3,4-tetrahydroisoquinolin)-2-yl-methyl]-imidazole dihydrochloride (Compound 27).

(i) 2-Phenyl-4(5)-2-phenyl-5,6,7,8-tetrahydrobenzimidazole imidazole dihydrochloride (Compound 76).

EXAMPLE IX

The following compounds were prepared essentially according to the procedures described in Examples I–VII:

(a) 2-(2,3-Dimethoxyphenyl)-4(5)-[(1,2,3,4-tetrahydroisoquinolin)-2-yl-methyl]-imidazole dihydrochloride (Compound 28), m.p. 205–207° C.

(b) 2-(4-Methoxyphenyl)-4(5)-[(N-methyl-N-benzyl) amninomethyl]-imidazole dihydrochloride (Compound 29).

(c) 2-(3,4-Dimethoxphenyl)-4(5)-[(N-methyl-N-benzyl) aminomethyl]-imidazole dihydrochloride (Compound 30).

(d) 2-(3-Methoxyphenyl)-4(5)-[(N-methyl) aminomethyl]-imidazole dihydrochloride (Compound 31).

(e) 2-(5-Chloro-2-methoxyphenyl)-4(5)-[(N-methyl-N-benzyl)ainomethyl]-imidazole (Compound 32), m.p. 88–89° C.

(f) 2-(5-Chloro-2-methoxyphenyl)-4(5)-[(N,N-dimethyl)aminomethyl]-imidazole dihydrochloride (Compound 33), m.p. 231–233° C.

(g) 2-(5-Chloro-2-methoxyphenyl)-4(5)-[(N-methyl)aminomethyl]-imidazole dihydrochloride (Compound 34), m.p. 225–227° C.

(h) 2-(5-Chloro-2-methoxyphenyl)-4(5)-[(N-benzyl)aminomethyl]-imidazole dihydrochloride (Compound 35), m.p. 184–186° C.

(i) 2-(5-Chloro-2-benzyloxyphenyl)-4(5)-[(N-methyl-N-benzyl)aminomethyl]-imidazole dihydrochloride (Compound 36), m.p. 118–123° C.

(j) 2-(2-Benzyloxyphenyl)-4(5)-[(N-methyl-N-benzyl)aminomethyl]-imidazole dihydrochloride (Compound 37), m.p. 199–200° C.

(l) 2-(3-Ethylphenyl)-4(5)-[(N-methyl-N-benzyl)aminomethyl]-imidazole dihydrochloride (Compound 38), m.p. 234–235° C.

(m) 2-(5-Chloro-2-methoxyphenyl)-4(5)-[(N-methyl-N-(-4-chlorobenzyl))aminomethyl]-imidazole dihydrochloride (Compound 39), m.p. 186–188° C.

(n) 2-(5-Chloro-2-hydroxyphenyl)-4(5)-[(N-methyl-N-benzyl)aminomethyl]-idazole dihydrochloride (Compound 40), m.p. 227–228° C.

(o) 2-(5-Bromo-2-benzyloxyphenyl)-4(5)-[(N-methyl-N-benzyl)aminomethyl]-imidazole dihydrochloride (Compound 41).

(p) 2-(5-Ethyl-2-methoxyphenyl)-4(5)-[(N-methyl-N-benzyl)aminomethyl]-imidazole dihydrochloride (Compound 42), m.p. 114–115° C.

(q) 2-(5-Chloro-2-methoxyphenyl)-4(5)-[(4-(2-methoxyphenyl)-piperazin-1-yl)-methyl]-imidazole dihydrochloride (Compound 43), m.p. 138–143° C.

(r) 2-(5-Chloro-2-methoxyphenyl)-4(5)-[(4-phenyl-pipendin-1-yl)-methyl]-imidazole dihydrochloride (Compound 44), m.p. 138–143° C.

(s) 2-Phenyl-4(5)-[(4-phenyl-piperazin-1-yl)methyl]imidazole (Compound 45), m.p. 189–191° C.

(t) 2-(4-Fluorophenyl)-4(5)[(4-phenyl-piperidin-1-yl)-methyl]-imidazole dihydrochloride (Compound 46), m.p. 260–264° C. (dec).

(u) 2-(4-Methoxyphenyl)-4(5)[(4-phenyl-piperidin-1-yl)-methyl]-imidazole dihydrochloride (Compound 47), m.p. 196–199° C.

(v) 2-Phenyl-4(5)-[(4-(3-trifluoromethylphenyl)-piperazin-1-yl-)methyl]imidazole (Compound 48), m.p. 182–184° C.

(w) 2-(2-Methoxyphenyl)-4(5)[(4-phenyl-piperidin-1-yl)-methyl]-imidazole dihydrochoride (Compound 49).

(x) 2-(3-Methoxyphenyl)-4(5)[(4-phenyl-piperidin-1-yl)-methyl]-imidazole dihydrochloride (Compound 50), m.p. 114–117° C.

(y) 2-(3-Fluorophenyl)-4(5)[(4-phenyl-piperidin-1-yl)-methyl]-imidazole (Compound 51), m.p. 110–112° C.

(z) 2-(2-Fluorophenyl)-4(5)[(4-phenyl-piperidin-1-yl)-methyl]-imidazole dimaleate (Compound 52), m.p. 142–144° C.

(aa) 2-(2-Methylphenyl)-4(5)-[(4-benzyl-piperidin-1-yl)-methyl]-imidazole dihydrochloride (Compound 53), m.p. 242–244° C.

(ab) 2-(5-Ethyl-2-methoxyphenyl-4(5)-[(4-phenyl-piperdin-1-yl)-methyl]-imidazole dihydrochloride (Compound 54), m.p. 76–78° C.

(ac) 2-(5-Ethyl-2-methoxyphenyl-4(5)-[(4-(2-methoxyphenyl)-piperazin-1-yl)-methyl]-imidazole dihydrochloride (Compound 55), m.p. 61–64° C.

(ad) 2-Phenyl-4(5)-[(4(4-fluorophenyl)-piperazin-1yl-)methyl]imidazole dihydrochloride (Compound 56), m.p. 64–68° C.

(ae) 2-(5-Ethyl-2-methoxyphenyl-4(5)-[(4-(2-pyrimidinyl)-piperazin-1-yl)-methyl]-imidazole dihydrochloride (Compound 57), m.p. 75–78° C.

(af) 2-Phenyl-4(5)-[(4(4-fluoro-2-pyrimidinyl)-piperazin-1yl)-methyl]imidazole dihydrochloride (Compound 58), m.p. 188–190° C.

(ag) 2-(4-Fluorophenyl)-4(5)-[(4-(2-pyrimidinyl)-piperazin-1-yl)-methyl]-imidazole dihydrochloride (Compound 59), m.p. 181–184° C.

(ah) 2-Phenyl-4(5)-[(4(5-chloro-2-methylphenyl)-piperazin-1yl-)-methyl]imidazole dihydrochloride (Compound 60), m.p. 142–145° C.

(ai) 2-Phenyl-4(5)-[(4(3,4-dichlorophenyl)-piperazin-1ly-)methyl]imidazole (Compound 61), m.p. 179–181° C.

(aj) 2-Phenyl-4(5)-[(4(4-fluorophenyl)-piperidin-1yl-)methyl]imidazole dimaleate (Compound 62), m.p. 148–149° C.

(ak) 2-(3-Fluorophenyl)-4(5)-[(4-benzyl-piperidin-1-yl)-methyl]-imidazole dimaleate (Compound 63), m.p. 148–149° C.

(al) 2-(4-Fluorophenyl)-4(5)-[(4-benzyl-piperidin-1-yl)-methyl]-imidazole dihydrochloride (Compound 64), m.p. 254–256° C.

(am) 2-Phenyl-4(5)-[(4-(4fluorobenzyl)-piperidin-1-yl)-methyl]-imidazole dihydrochloride (Compound 65).

(an) 2-(2-Fluorophenyl-4(5)-[(4-(2-pyrimidinyl)-piperazin-1-yl)-methyl]-imidazole (Compound 66), m.p. 159–161° C.

(ao) 2-(4-Methylphenyl-4(5)-[(4-(2-pyrimidinyl)-piperazin-1-yl)-methyl]-imidazole (Compound 67), m.p. 176–179° C.

(ap) 2-(2-Fluorophenyl)-4(5)-[(4-benzyl-piperidin-1-yl)-methyl]-imidazole dimaleate (Compound 68), m.p. 113–115° C.

(aq) 2-(4-Chlorophenyl-4(5)-[(4-(2-pyridyl)-piperazin-1-yl)-methyl]-imidazole (Compound 69), m.p. 176–177° C.

(ar) 2-Phenyl-4(5)-[(4-(4-fluoro-2-pyrimidinyl)-piperazin-1-yl)-methyl]-imidazole dimaleate (Compound 70), m.p. 185–186° C.

(as) 2-(2-Fluorophenyl-4(5)-[(4-(4-fluoro-2-pyrimidinyl)-piperazin-1-yl)-methyl]-imidazole dimaleate (Compound 71), m.p. 172–173° C.

(at) 2-(4-Fluorophenyl-4(5)-[(4-(4-fluoro-2-pyrimidinyl)-piperazin-1-yl)-methyl]-imidazole dimaleate (Compound 72), m.p. 183–184° C.

EXAMPLE X (Compound 73)

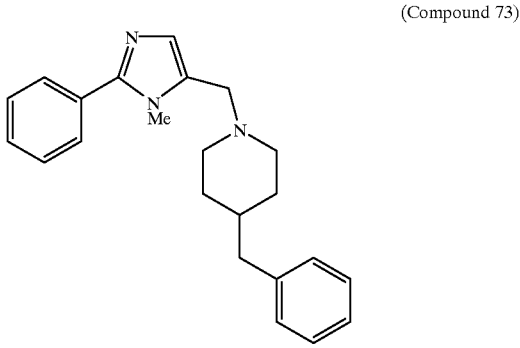

A solution of 40 mL tetrahydrofuran containing 1.0 g of 2-phenylimidazole was cooled to 0° C. and 4 mL of 2M lithium diisopropylamide was added dropwise which resulted in the formation of a white suspension. The mixture was stirred for 10 min at 0° C. and then 0.7 mL of dimethyl sulfate was added The reaction was allowed to stir at room temperature for an additional 30 min during which time the solution became homogeneous. Aqueous ammonium chloride was added and the tetrahydrofuran was removed by evaporation under reduced pressure. The aqueous phase was extracted with 2×100 mL aliquots of dichloromethane. The combined organic extracts were washed with dilute ammonium hydroxide and brine. The combined organic extracts were dried over anhydrous sodium sulfate and concentrated under reduced pressure to yield 1 g of 1-methyl-2-phenylimidazole which was used in the next step without further purification or characterization.

To a solution of 1 g of 1 methyl-2-phenylimidazole in 10 mL acetic acid were added 0.4 mL of 37% aqueous formaldehyde and 1.2 mL of 4-benzylpiperidine. The reaction mixture was heated at 100° C. for 10 hours and the acetic acid then removed by evaporated under reduced pressure. The residue was dissolved in water and made alkaline with 5% sodium hydroxide and extracted with 2×100 mL of dichloromethane. The combined extracts were dried over anhydrous sodium sulfate and concentrated to small volume under reduced pressure to give 1 methyl-2-phenyl-4-[(4-benzylpiperidin-1-yl)methyl]-imidazole.

The following compounds were prepared essentially according to the procedure described in Example X utilizing 2-phenyl-4(5)-[(4-(2-pyrimidinyl)piperazin-1-yl) methylimidazole (Compound 22) as starting material. The resulting isomers were separated by chromatography on silica gel using ethyl acetate as eluant.

a) 1-Methyl-2-phenyl-4[(4-(2-pyrimidinyl)piperazin-1-yl)methyl]-imidazole (Compound 74).

b) 1-Methyl-2-phenyl-5-[(4-(2-pyrimidinyl)piperazin-1-yl)methyl]-imidazole (Compound 75).

EXAMPLE XI

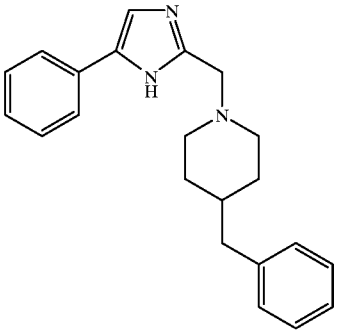

A mixture of 3 g of ethylthiooxamate, 4.25 g of 2-aminoacetophenone hydrochloride and 3.69 g of sodium acetate was dissolved in 20 mL of acetic acid and heated under reflux for 3 hr. The reaction mixture was allowed to cool to room temperature and the acetic acid removed by evaporation under reduced pressure. The residue was basified with aqueous sodium carbonate and extracted with 2×100 mL of ethyl acetate. The combined extracts were washed with 2×100 mL of brine, dried over anhydrous sodium sulfate and the solvent removed under reduced pressure to yield 2.8 g of ethyl 4-phenylimidazole-2-carboxylate as a solid which was used in the next step without further purification or characterization.

To a solution of 2.75 g ethyl-4-phenylimidazole-2-carboxylate in 20 mL tetrahydrofuran was added a suspension of 0.5 g lithium aluminum hydride in 30 mL of tetrahydrofuran. The reaction mixture was stirred at room temperature overnight, poured into 100 mL of ice water and extracted with 2×100 mL of ethyl acetate. The combined extracts were washed with 2×100 mL of brine, dried over anhydrous sodium sulfate and the solvent removed under reduced pressure to yield 2 g of 2-hydroxymethyl-4-phenylimidazole which was used in the next step without further purification or characterization.

A solution of 1 g of 2-hydroxymethyl-4-phenylimidazole in 10 mL of thionyl chloride was heated at 60° C. for 1 hr. After removal of excess thionyl chloride by evaporation under reduced pressure, the residue was treated with a solution of 1 g 4-benzylpiperidine and 2 g N,N,-diisopropylethylamine in 50 mL of chloroform. The reaction mixture was stirred at 60° C. for 1 hr, allowed to cool to room temperature and washed successively with 50 mL of 1N sodium hydroxide solution and 50 mL of water. The organic phase was then dried over anhydrous sodium sulfate and the solvent evaporated under reduced pressure to yield 850 mg of 4-phenyl-2(5)-[(4-benzylpiperidin-1-yl)-methyl] imidazole which was converted into its monofumarate salt (Compound 77), m.p 155–157° C.

EXAMPLE XII

The following compounds were prepared essentially according to the procedure described in Example XII.

(a) 4-Phenyl-2(5)-[(N-methyl-N-benzyl)aminomethyl]-imidazole dihydrochloride (Compound 78), m.p. 229–231° C.

(b) 4-Phenyl-2(5)-[(4-(2-pyrimidinyl)-piperazin-1-yl)-methyl]-imidazole dihydrochloride (Compound 79), m.p. 178–180° C.

(c) 4-Phenyl-2(5)-[4-(4-fluoro-benzyl-piperdin-1-yl)-methyl]-imidazole dihydrochloride (Compound 80), m.p. 216–218° C.

(d) 4-Phenyl-2(5)-[(4-phenyl-piperidin-1-yl)-methyl]-imidazole dihydrochloride (Compound 81), m.p. 182–184° C.

(e) 4-Phenyl-2(5)-[(4-(4-fluorophenyl)-piperazin-1yl-)methyl]imidazole dihydrochloride (Compound 82), m.p. 161–163° C.

(f) 4-Phenyl)-2(5)-[(4-(2-methoxyphenyl)-piperazin-1-yl)-methyl]-imidazole dihydrochloride (Compound 83), m.p. 229–231° C.

(g) 4-Phenyl-2(5)-[(4-(2-pyridyl)-piperazin-1-yl)-methyl]-imidazole trihydrochloride (Compound 84), m.p. 165–167° C.

(h) 4-Phenyl-2(5)-[(4-phenyl-piperazin-1yl-)methyl]imidazole dihydrochloride (Compound 85), m.p. 182–184° C.

(i) 4-Phenyl-2(5)-[(4-benzoyl-piperidin-1-yl)-methyl]-imidazole dihydrochloride (Compound 86) m.p. 200–202° C.

(j) 4-Phenyl-2(5)-[4-fluoro-benzoyl-piperidin-1-yl)-methyl]-imidazole dihydrochloride (Compound 87), m.p. 173–175° C.

EXAMPLE XIII

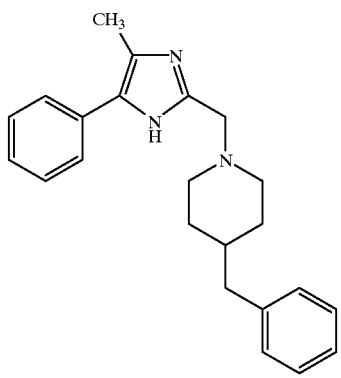

A solution of 10 g of 2-bromopropiophenone in 50 mL fornamide was heated at 180° C. overnight The reaction was then allowed to cool to room temperature and poured into 250 mL ice water. The mixture was adjusted to pH 9 with 1N sodium hydroxide and the resulting precipitate was collected by filtration, washed with water and dried to yield 6.0 g of 4-methyl-5-phenylimidazole as a solid which was used in the next step without further purification.

A mixture of 128 mg 4-methyl-5-phenylimidazole, 180 mg of 4-benzylpiperidine and 85 mg of 37% formaldehyde in 10 mL acetic acid was heated under reflux for 8 hr. The acetic acid was then removed by evaporation under reduced pressure and the residue was dissolved in 50 mL ethyl acetate. The ethyl acetate solution was washed successively with 50 mL of dilute sodium hydroxide solution and water. The ethyl acetate extract was then dried over anhydrous sodium sulfate and the solvent removed by evaporation under reduced pressure to yield 5-methyl-4-phenyl-2(5)-[(4-benzyl-piperidin-1-yl)-methyl]imidazole as an oil which was purified by chromatography on silica gel using 5% methanol in methylene chloride as eluent. Treatment of the purified free base with ethanolic HCl yielded 5-methyl-4-phenyl-2(5)-[(4-benzylpiperidin-1-yl)-methyl]imidazole dihydrochloride (Compound 88).

EXAMPLE XIV

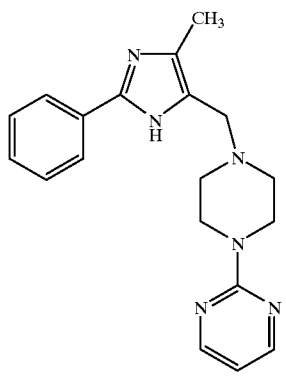

To a solution of 14.3 g 2-phenyl-4(5)-methylimidazole and 13.8 g of 1-(2-pyrimidyl)piperazine in 50 mL of ethanol was added a solution of 7.1 mL of aqueous formaldehyde. The resulting mixture was heated at reflux temperature for 2 hr and allowed to cool to room temperature. The solid was collected by filtration and dried to yield 20 g of 2-phenyl-5-methyl-4(5)-[(4-(2-pyrimidinyl)piperazin-1-yl)methyl]imidazole which was treated with 2 equivalents of maleic acid in isopropanol to yield 2-phenyl-5-methyl-4(5)-[(4-(2-pyrimidinyl)piperazin-1-yl)methyl]-imidazole dimaleate (Compound 89), m.p. 172–174° C.

EXAMPLE XV

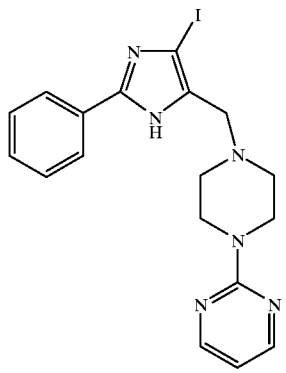

To a solution of 100 mg of 2-phenyl-4(5)-[(4-(2-pyrimidinyl)piperazin-1-yl)methyl]imidazole in 10 mL of chloroform was added one equivalent (80 mg) of iodine in 5 mL of chloroform followed by 0.5 mL of triethylamine. The reaction mixture was stirred at room temperature for 30 min during which time a solid crystallized from the solution. The solid was collected by filtration to yield 52 mg of 2-phenyl-5-iodo-4(5)-[(4-(2-pyrimidinyl)piperazin-1-yl)methyl]-imidazole hydroiodide salt (Compound 90) which had a m.p. of 196–199° C.

EXAMPLE XVI

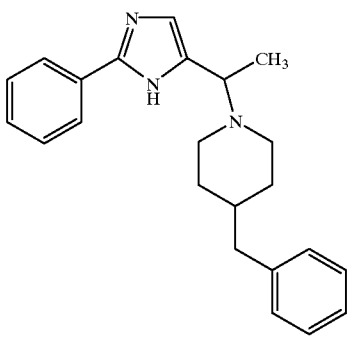

To a solution of 220 mg of 2-phenyl-4-imidazole carboxaldehyde in 5 mL of tetrahydrofuran was added 6.4 mL of a 1L methyllithium solution in tetrahydrofuran. The reaction mixture was quenched with 50 mL of water and the mixture extracted with 2×50 mL aliquots of ethyl acetate. The combined ethyl acetate extracts were dried over anhydrous sodium sulfate, filtered and the solvent evaporated under reduced pressure to yield 250 mg of 2-phenyl-4(5)-(1-hydroxyethyl)imidazole which was used in the next step without further purification or characterization. The residue of 2-phenyl-4(5)-(1-hydroxyethyl)imidazole was dissolved in 8 mL of thionyl chloride and heated at reflux temperature for 30 min after which the thionyl chloride was removed by distillation under reduced pressure to yield 250 mg of 2-phenyl-4(5)-(1-chloroethyl)imidazole as an oil which was used in the next step without additional purification or characterisation. This oil was dissolved in 10 mL of chloroform and to this solution was added 224 mg of 4 benzylpiperidine and 2 mL of triethylamine. The reaction was allowed to stand at room temperature for 10 min and then washed with 50 mL 1N sodium hydroxide. The chloroform extract was then separated and dried over anhydrous sodium sulfate, filtered and the solvent removed by evaporation under reduced pressure to yield 2-phenyl-4(5)-[1-((4-benzyl-piperidin-1-yl)-ethyl)]imidazole which was purified by chromatography on silica gel using 10% methanol/dichloromethane as eluent. Treatment with ethanolic HCl yielded 2-phenyl-4(5)-[1-((4-benzyl-piperidin-1-yl)-ethan-1-yl)]imidazole dihydrochoride salt Compound 91), m.p. 169–171° C.

EXAMPLE XVII

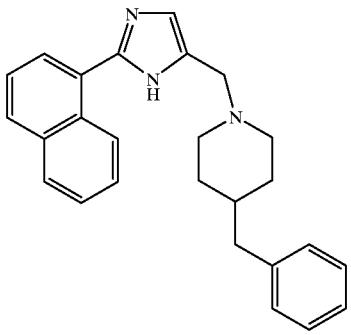

A solution of 5.5 g 1-cyanonaphthalene in 150 mL dry ether was cooled to 0° C. To this solution 12.1 g lithium bis(trimethylsilyl)amide was added in one portion. The mixture was stirred for 12 hours and allowed to warm to room temperature. The reaction mixture was cooled to 0° C. then quenched by the addition of 200 mL 3N HCl. After siring 20 minutes at 0° C., the mixture was transferred to a separatory funnel and washed 3×100 mL ether. The aqueous layer was cooled on an ice bath and adjusted to pH 14 with solid sodium hydroxide. This solution was extracted 4×100 mL dichloromethane. The combined organic extracts were washed 2×100 mL water, 1×100 mL brine, dried over potassium carbonate, filtered, then concentrated under reduced pressure to give 3.6 g of the desired amidine which was used without further purification.

A mixture of 3.6 g of the crude amidine, 2.5 g of dihydroxyacetone dimer, and 2.5 g of ammonium chloride were suspended in 35 mL conc. ammonium hydroxide in a pressure tube. The mixture was heated to 90° C. for 3 hours during which time the amidine dissolved and the product precipitated out. The reaction mixture was cooled to room temperature and the product collected by filtration, washed with cold water, and dried in vacuo to give 3 g 2-(1-naphthyl)-4(5)-(hydroxymethyl)imidazole as off-white crystals, m.p. 155–158° C.

A solution of 62 mg 2-(1-naphthyl)-4(5)-(hydroxymethyl) imidazole was dissolved in 3 mL of thionyl chloride and warmed to 60° C. for 2 hours. The solvent was removed and the residue was dissolved in 3 mL chloroform and 53 mg 4-benzylpiperidine was added followed by 47 mg of diisopropylethylamine. The reaction mixture was stirred at room temperature for 1 hour, diluted with 3 volumes of chloroform, then washed 3×3 mL of 10% sodium hydroxide. The organic layer was dried over anhydrous sodium sulfate, filtered, then concentrated under reduced pressure. The residue was purified by chromatography on silica gel eluting with 5% methanol in dichloromethane to yield 62 mg of 2-(1-naphthyl)-4(5)-[(4-benzyl-piperidin-1-yl)-methyl] imidazole (Compound 92), m.p. 81–83° C.

EXAMPLE XVIII

The following compounds were prepared from the corresponding nitriles essentially according to the procedures described in Example XVII.

(a) 2-(1-Naphthyl)-4(5)-[(4-(2-pyrimidinyl)-piperazin-1-yl)-methyl]-imidazole (Compound 93), m.p. 187–188° C.

(b) 2-(1-Naphthyl)-4(5)-[(4-(2-pyridyl)-piperazin-1-yl)-methyl]-imidazole (Compound 94), m.p. 182–183° C.

(c) 2-(1-Naphthyl)-4(5)-[(N-methyl-N-benzyl)-methyl]-imidazole (Compound 95), m.p. 74–76° C.

(d) 2-(2-Naphthyl)-4(5-[(4-benzyl-piperidin-1-yl)-methyl]-imidazole (Compound 96), m.p. 92–94° C.

(e) 2-(2-Naphthyl)-4(5)-[(4-(2-pyrimidinyl)-piperazin-1-yl)-methyl]-imidazole (Compound 97), m.p. 218–219° C.

(f) 2-(2-Naphthyl)-4(5)[(4-(2-pyridyl)-piperazin-1-yl)-methyl]-imidazole (Compound 98), m.p. 199–201° C.

(g) 2-(2-Naphthyl)-4(5)-[(N-methyl-N-benzyl)-methyl]-imidazole (Compound 99), m.p. 86–87° C.

(h) 2-(2-Pyridyl)-4(5)-[(4-benzyl-piperidin-1-yl)-methyl]-imidazole (Compound 100), m.p. 96–98° C.

(i) 2-(2-Pyridyl)-4(5)-[(4-(2-pyrimidinyl)-piperazin-1-yl)-methyl]-imidazole (Compound 101), m.p. 134–135° C.

(j) 2-(2-Pyridyl)-4(5)-[(4-(2-pyridyl)-piperazin-1-yl)-methyl]-imidazole (Compound 102), m.p. 135–137° C.

(k) 2-(2-Pyridyl)-4(5)-[(N-methyl-N-benzyl)-methyl]-imidazole (Compound 103), m.p. 61–63° C.

(l) 2-(3-Pyridyl)-4(5)-[(4-(2-pyrimidinyl)-piperazin-1-yl)-methyl]-imidazole (Compound 104), m.p. 155–157° C.

(m) 2-(3-Pyridyl)-4(5)-[(N-methyl-N-benzyl)-methyl]-imidazole (Compound 105), m.p. 141–142° C.

(n) 2-(4-Pyridyl)-4(5)-[(4-(2-pyrimidinyl)-piperazin-1-yl)-methyl]-imidazole (Compound 106), m.p. 154–156° C.

(o) 2-(2-Pyrazinyl)-4(5)-[(4-benzyl-piperidin-1-yl)-methyl]-imidazole (Compound 107), m.p. 80–81° C.

(p) 2-(2-Pyrazinyl)-4(5)-[(4-(2-pyrimidinyl)-pipenzin-1-yl)-methyl]-imidazole (Compound 108), m.p. 164–165° C.

(q) 2-(2-Pyrazinyl)-4(5)-[(N-methyl-N-benzyl)-methyl]-imidazole (Compound 109), m.p. 93–94° C.

(r) 2-(2-Thienyl)-4(5)-[(4-benzyl-piperidin-1-yl)-methyl]-imidazole (Compound 110), m.p. 77–79° C.

(s) 2-(2-Thienyl)-4(5)-[(4)-(2-pyrimidinyl)-piperazin-1-yl)-methyl]-imidazole (Compound 111), m.p. 204–205° C.

(t) 2-(2-Thienyl)-4(5)-[(N-methyl-N-benzyl)-methyl]-imidazole (Compound 112), m.p. 132–134° C.

(u) 2-(2-Thienyl)-4(5)-[(4-(2-pyridyl)-piperazin-1-yl)-methyl]-imidazole (Compound 113), m.p. 179–181° C.

(v) 2-(2-Quinolinyl)-4(5)-[(4-(2-pyrimidinyl)-piperazin-1-yl)-methyl]-imidazole (Compound 114), m.p. 263° C. (dec).

(w) 2-(2-Quinolinyl)-4(5)-[(N-methyl-N-benzyl)-methyl]-imidazole (Compound 115), m.p. 247° C. (dec).

EXAMPLE XIX

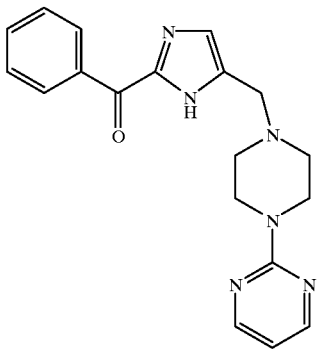

A solution was prepared by dissolving 193 mg of 2-benzoylimidazole, 330 mg of 1-(2-pyrimidyl)-piperazine and 165 mL of a 37% solution of formaldehyde in 1 mL of acetic acid and the resulting mixture was heated to 100° C. for 15 hours. The mixture was then cooled to 0° C., basified with 3 N hydrochloric acid, then extracted with 5×10 mL of ethyl acetate. The organic extracts were washed with 2×10 mL water, 1×10 mL of brine, dried over anhydrous sodium sulfate, filtered, then concentrated under reduced pressure. The residue was chromatographed on silca gel using 5% methanol in dichloromethane as eluent to yield 43 mg of 2-(benzoyl)-4(5)-[(4-(2-pyrimidinyl)-piperazin-1-yl)-methyl]-imidazole (Compound 116), m.p. 177–179° C.

EXAMPLE XX

The following compounds were prepared essentially according to the procedures described in Example XVII.

a) 2-Benzyl-4(5)-[(4-(2-pyrimidinyl)-piperazin-1-yl)-methyl]-imidazole (Compound 117), m.p. 160–161° C.

(b) 2-(5-Methoxy-3,4dihydro-naphth-1-yl)-4(5)-[(N-methyl-N-benzyl)-methyl]-imidazole (Compound 118), m.p. 133–134° C.

EXAMPLE XXI

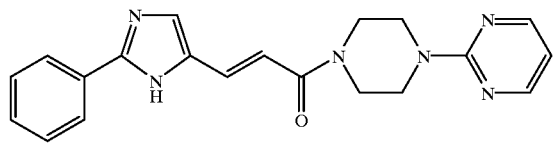

A solution of 1.25 g of 2-phenyl-4(5)-imidazole propenoic acid was dissolved in 20 mL thionyl chloride and heated at reflux temperature for 2 hours. The solvent was removed and the residue suspended in 20 mL chloroform. To this solution was added 1.7 g of 1-(2-pyrimidinyl)-piperazine dihydrogen chloride followed by 3.5 mL of diisopropylethylamine. The reaction mixture was stirred for 6 hours at room temperature then diluted with 50 mL chloroform, washed with 3×20 mL of 10% sodium hydroxide solution, dried over anhydrous sodium sulfate, filtered and concentrated under reduced pressure. The residue was chromatographed on silica gel using 5% methanol in dichloromethane as eluent to yield 554 mg of 2-phenyl-4(5)-[(4 (2-pyrimidinyl)-piperazin-1-yl)-propen-1-oyl]-imidazole (Compound 119), m.p. 235–236° C.

EXAMPLE XXII

The following compounds were prepared according to the procedure described in Example XXI:

(a) 2-Phenyl-4(5)[(4-phenyl-piperazin-1-yl)-propen-1-oyl]-imidazole (Compound 120), m.p. 151–152° C.

(b) 2-Pheny-4(5)-[(4-hydroxy-4-(4-chlorophenyl)-piperidin-1-yl)-propen-1-oyl]-imidazole (Compound 121), m.p. 236–240° C.

EXAMPLE XXIII

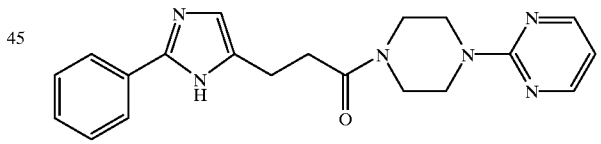

A solution of 68 mg 2-phenyl-4(5)-[(4-(2-pyrimidinyl)-piperazin-1-yl)-propen-1-oyl]-imidazole was dissolved a mixture of in 2 ml ethyl acetate and 0.2 ml ethanol and the suspension was stirred for 2 days under a $H_2$ atmosphere, using 20 mg Pt on carbon as catalyst. The mixture was filtered through Celite and the solvent removed The residue was chromatographed on silca gel using 5% methanol/dichloromethane as eluent to yield 37 mg 2-phenyl-4(5)-[(4-(2-pyrimidinyl)-piperazin-1-yl)-propan-1-oyl]-imidazole (Compound 122), m.p. 143–148° C.

EXAMPLE XXIV

The following compounds were prepared according to the procedure described in EXAMPLE XXIII (a) 2-Phenyl-4(5)-[(4-phenyl-piperazin-1-yl)-propan-1-oyl]-imidazole (Compound 123), m.p. 180–183° C.

(b) 2-Phenyl-4(5)-[(4-(2-(3,4,5,6-tetrahydro)-pyrimidinyl)-piperazin-1-yl)-propan-1-oyl]-imidazole (Compound 124), m.p. 210–211° C.

EXAMPLE XXV

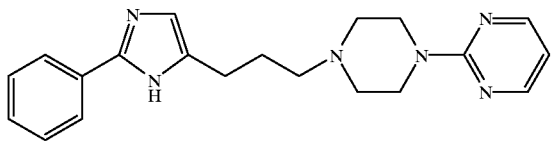

To a solution of 84 mg 2-phenyl-4(5)-[(4-(2-pyrimidinyl)-piperazin-1-yl)-propan-1-oyl]-imidazole in 5 mL dry tetrahydrofuran at room temperature was added 18 mg of lithium aluminum hydride and the mixture was heated at reflux temperature refluxed for 2 hours. After quenching with ethyl acetate, the solvent was removed under reduced pressure. The residue was chromatographed on silca gel using 10% methanol in dichloromethane as eluent to yield 20 mg of 2-phenyl-4(5)-[(4-(2-pyrimidinyl)-piperzin-1-yl)-propan-1-yl]-imidazole (Compound 125), m.p. 133–135° C.

EXAMPLE XXVI

The following compounds were prepared according to the procedure described in Example XXV.
(a) 2-Phenyl-4(5)-[(4-phenyl-piperazin-1-yl)-propan-1-yl]-imidazole (Compound 126), m.p. 50–54° C.
(b) 2-Phenyl-4(5)-[(4-hydroxy-4-(4-chlorophenyl)-piperidin-1-yl)-propan-1-yl]-imidazole (Compound 127), m.p. 122–124° C.

EXAMPLE XXVII

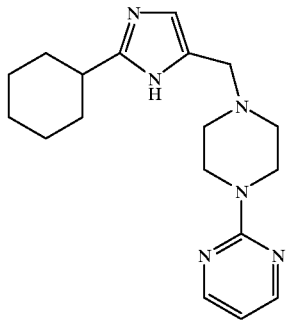

To a solution of 6.8 g of 2-phenylimidazole in 200 mL 3N hydrochloric acid was added 5% Rhodium on Carbon, Degussa type G10 NB/W. The mixture was hydrogenated at 100 psi for 24 hours then filtered through celite. The solution was neutralized with 25% sodium hydroxide and extracted with 2×100 mL ethyl acetate. The combined extract was washed with 200 mL of brine and dried over anhydrous sodium sulfate. Evaporation of the solvent gave 2-cyclohexylimidazole as a fluffy, white solid which was used in the next step without further purification or characterization.

To a solution of 251 mg 2-cyclohexylimidazole in 8 mL of acetic acid, 274 mg of 1-(2-pyrimidyl)piperazine and 88 microliters of 37% formaldehyde were added The solution was heated at 100° C. for 12 hours then the solvent was removed under reduced pressure and the residue was diluted with water. The mixture was made slightly alkaline with 5% sodium hydroxide and then extracted with 2×25 mL of ethyl acetate. The combined extracts were washed with 25 mL of brine, dried over anhydrous sodium sulfate and the solvent removed by evaporation under reduced pressure. The products were separated on reverse phase silica gel (Whatman PLKC18F) using 0.2 M aqueous sodium chloride with 80% methanol Evaporation of the individual fractions yielded 2-cyclohexyl-4(5)-hydroxymethyl imidazole and 50 mg of the desired 2cyclohexyl-4(5)-[(4-(2-pyrimidinyl)-piperazin-1-yl)-methyl]-imidazole (Compound 128), m.p. 210–213° C.

EXAMPLE XXVIII

The following compounds were prepared essentially according to the procedure described in Example XXVII.
(a) 2-cyclohexyl-4(5)-[(4-benzyl-piperidin-1-yl)-methyl]-imidazole (Compound 129), m.p. 185–188° C.
(b) 2-cyclohexyl-4(5)-[(N-methyl-N-benzyl)-methyl]-imidazole (Compound 130), m.p. 235–238° C.
(c) 2-(4-methylcyclohexyl)-4(5)-[(4-(2-pyrimidinyl)-piperazin-1-yl)-methyl]-imidazole (Compound 131).

EXAMPLE XXIX

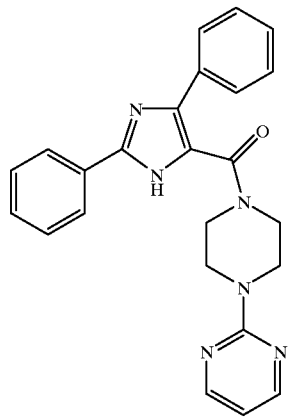

A solution of 790 mg of iodine in 5 mL of chloroform was added to 1.0 g of 2-phenyl-4(5)-[(4-(2-pyrimidinyl)piperazin-1-yl)methyl]imidazole dissolved in 30 mL of chloroform at ambient temperature. After the solution was stirred for 10 minutes 1 mL of triethylamine was added and stirring was continued until no more solids formed. The solid was collected by filtration and after drying yielded 700 mg of 2-phenyl-5-iodo-4(5)-[(4-(2-pyrimidinyl)piperazin-1-yl)methyl]-imidazole which was used in the next step without further purification or characterization.

To a solution of 53 mg 2-phenyl-5-iodo-4(5)-[(4-(2-pyrimidinyl)piperazin-1-yl)methyl]-imidazole in 1 mL of dimethylformamide was added 130 microliters of phenyltrimethylstannane and 3 mg of bis(triphenylphosphine)-palladium(II) chloride. The reaction mixture was heated at 100° C. for 4 hours then poured into water and extracted with 2×10 mL of ethyl acetate and washed with 10 mL of 10% ammonium hydroxide. The combined organic extracts were dried over anhydrous sodium sulfate and the solvent removed by evaporation under reduced pressure. The resulting material was chromatographed on silica gel with 5% methanol in dichloromethane as eluant to yield 15 mg of 2,5-diphenyl-4(5)-[(4-(2-pyrimidinyl)piperazin-1-yl)methyl]-imidazole (Compound 132), m.p. 221–225° C.

EXAMPLE XXX

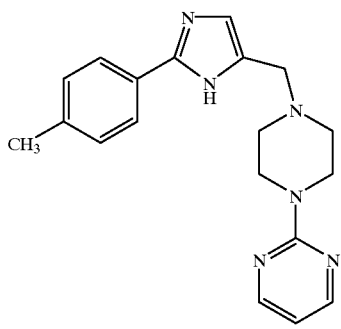

To a solution of 12.4 g p-tolunitrile in 500 mL of diethyl ether was added 23 g of solid lithium bis(trimethylsilyl) amide at ambient temperature. The mixture was stirred for 2 hours then hydrolysed with 10% HCl at 0° C. The mixture was stirred for an additional 30 minutes and then concentrated to dryness to yield 6 g of 4-methylbenzamidine hydrochloride which was used in the next step without further purification A solution of 4 g 4-methylbenzamidine hydrochloride in 60 mL ammonium hydroxide was treated with 4.0 g with dihydroxyacetone and 4.8 g ammonium chloride. The reaction mixture was heated to 90° C. for 4 hours in a sealed tube. On cooling to room temperature a the solid formed was collected by filtration to yield 3.0 g 2-(4-methylphenyl)-5-hydroxymethyl-imidazole which was converted according to the procedure described in Example VII to yield 2-(4-methylphenyl-4(5)-[(4-(2-pyrimidinyl)-piperazin-1-yl)-methyl]-imidazole (Compound 133), m.p. 178–180° C.

EXAMPLE XXXI

The following compounds were prepared according to the procedure described in Example XXX.

(a) 2-(4-Iodophenyl-4(5)-[(4-(2-pyrimidinyl)-piperazin-1-yl]-methyl)-imidazole (Compound 134), m.p. 218–220° C.

(b) 2-Phenyl-4(5)[(4-(4-chlorophenyl)-3-methylpiperazin-1-yl)methyl]imidazole (Compound 135), m.p. 137–139° C.

(c) 2-Phenyl-4(5)-[(4-(4-methylphenyl)-3-methylpiperazin-1-yl)methyl]imidazole (Compound 136), m.p. 172–174° C.

(d) 2-Phenyl-4(5)-[(4-(4-methoxyphenyl)-3-methylpiperazin-1-yl)methyl]imidazole (Compound 135), m.p. 188–190° C.

EXAMPLE XXXII

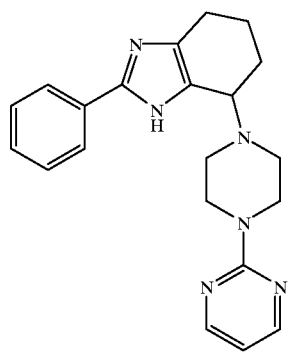

To a solution of 6.3 g benzaimidine hydrochloride in 60 mL ammonium hydroxide was added 4.6 g 2-hydroxycyclohexanone. The reaction mixture was heated to 90° C. for 7 hours in a sealed tube. On cooling to room temperature the crystals formed were collected by filtration and after drying yielded 3.0 g 2-phenyl-4,5,6,7,-tetrahydrobenzimidazole (Compound 136), m.p. 300–301° C.

To a solution of 50 mg 2-phenyl-5,6,7,8-tetrahydrobenzimidazole in 5 mL carbon tetrachloride was added 40 mg 1,3-dibromo-5,5-dimethylhydantoin. The mixture was heated to reflux and irradiated with a 500W Tungsten lamp for 30 min. The temperature was lowered momentarily and a solution of 41 mg 1-(2-pyrimidyl) piperazne was added to the reaction. The mixture was again heated at reflux temperature for 30 min. Then 0.5 mL triethylamine was added to the reaction and the solution was stirred for 1 hour at room temperature. The volatiles were evaporated under reduced pressure and the product was purified on silica gel with 10% methanol in dichloromethane to yield 28 mg 2-phenyl-7-[(4-(2-pyrimidinyl)-piperazin-1-yl)-methyl]-4,5,6,7-tetrahydrobenzimidazole (Compound 137), m.p. 200–202° C.

EXAMPLE XXXIII

The following compounds were prepared according to the procedure described in Example XXXII.

(a) 2-phenyl-7-[(4-benzyl-piperidin-1-yl)-methyl]-4,5,6,7-tetrahydrobenzimidazole (Compound 138), m.p. 189–191° C.

(b) 2-phenyl-7-[(N-methyl-N-benzyl)aminomethyl]-4,5,6,7-tetrahydrobenzimidazole (Compound 139), m.p. 181–183° C.

EXAMPLE XXXIV

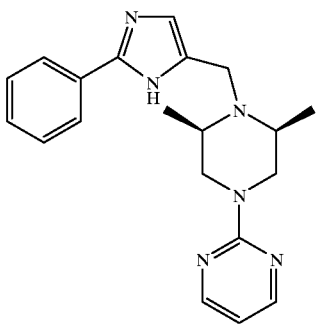

A solution of 820 mg 2-chloropyrimidine and 1.6 g cis-2,6-dimethylpiperazine in 25 mL toluene was heated at reflux temperature for 12 hours. The solvent was evaporated, the residue was basified with 5% sodium hydroxide and extracted with 2×100 mL of dichloromethane. The combined organic extracts were dried over anhydrous sodium sulfate and concentrated to give cis-2,6-dimethyl-1-(2-pyrimidyl)-piperazine. This amine was then used to prepare 2-phenyl-4(5)-[(4-(2-pyrimidinyl)-cis-2,6-dimethylpiperazin-1-yl)-methyl]-imidazole (Compound 140), m.p. 130–135° C., according to the procedures described in Example VIII.

EXAMPLE XXXV

The following compounds were prepared according to the procedure described in Example XXXIV.

(a) 2-phenyl-4(5)-[(4-(2-pyrimidinyl)-trans-2,5-dimethylpiperazin-1-yl)-methyl]-imidazole (Compound 141), m.p. 175–178° C.

(b) 2-phenyl-4(5)-[(8-(2-pyrimidinyl)-3-8-diazabicyclo(3.2.1)octan-3-yl)-methyl]-imidazole (Compound 142), m.p. 190–194° C.

EXAMPLE XXXVI

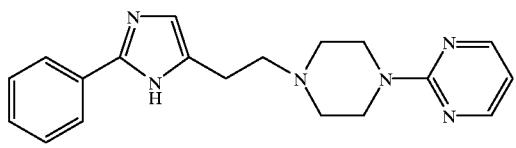

A mixture of 5.0 g 1,4-dihydroxy-2-butanone and 7.5 g benzamidine dihydrochloride in 70 mL ammonium hydroxide was heated to 90° C. for 5 hours in a sealed tube. The reaction mixture was diluted with 100 mL water, extracted with 2×50 mL chloroform, dried over anhydrous sodium sodium sulfate and the solvent removed by evaporation under reduced pressure. The residue was chromatographed on silica gel using 10% methanol in dichloromethane as eluent to yield 1.0 g 2-phenyl-4(5)-hydroxyethylimidazole which was reacted with 1-(2-pyrimidyl)piperazine according to the procedure Example VIII to yield 2-phenyl-4(5)-[(4-(2-pyrimidinyl)-piperazin-1-yl)-ethan-1-yl]-imidazole (Compound 143), m.p. 142–144° C.

EXAMPLE XXXVII

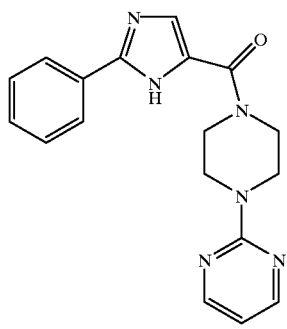

A mixture of 77 mg 2-phenylimidazole-4(5)-carboxylic acid and 5 mL of thionyl chloride was heated at reflux temperature for 1 hr. The thionyl chloride was removed under reduced pressure to yield 75 mg of 2-phenylimidazole-4-carboxylic acid chloride which was then dissolved in 5 mL chloroform and treated with 67 mg 1-(2-pyrimidyl)piperazine. The solution was heated at reflux temperature for 1 hr and then 0.5 mL triethylamine was added. The solution was stirred for another hour, concentrated under reduced pressure and the residue chromatographed on silica gel using 10% methanol in dichloromethane as eluent to yield 50 mg 2-phenyl-4(5)-N-[(4-(2-pyrimidinyl)-piperazin-1-yl)-carboxamido]-imidazole (Compound 144), m.p. 231–232° C.

EXAMPLE XXXVIII

The following compounds were prepared according to the procedure described in Example XXXVII.

(a) 2-phenyl-4(5)-N-[(N-methyl-N-benzyl)-carboxamido]-imidazole (Compound 145), characterized as oxalate salt, m.p. 198–199° C.

(b) 2-phenyl-4(5)-N-[(4-benzyl-piperidin-1-yl) carboxamido]-imidazole (Compound 146), characterized as the hydrochloride salt, m.p. 179–181° C.

EXAMPLE XXXIX

The following compounds were assayed for D2, D3, and D4 receptor binding activity using the assays described above.

| | Receptor Binding Activity (Ki, nM) | | |
|---|---|---|---|
| | Dopamine Receptor | | |
| Compound No. | D2 | D3 | D4 |
| 45 | 239 | 169 | 5 |
| 23 | 1033 | 8200 | 2.7 |
| 24 | 1029 | 123 | 0.85 |

EXAMPLE XXXX

Summary

The effects of 2-phenyl-4(5)-[(4-(2-pyrimidyl)-piperazin-1-yl)methyl]-imidazole dihydrochloride (Compound 23) and clozapine were evaluated in the following models of learning and memory: a step-down passive avoidance task assay and a modified Morris water maze assay Separate groups of male Sprague Dawley rats were pretreated with either Compound 23 or clozapine prior to training in these tasks. The control compound, clozapine, produced an acquisition deficit in the passive avoidance task at the two highest doses tested (1.0, 2.0 mg/kg) but produced no significant deficits in retention. Clozapine produced no deficits in the water maze task at the doses tested In the step-down passive avoidance assay animals that received the 0.25 mg/kg dose of Compound 23 showed significant improvement in memory compared to the vehicle group. Likewise in the modified Morrs water rraze, animals that received the 0.03, 0.25 and the 1.0 mg/kg dose of Compound 23 showed significant improvement in task retention compared to the vehicle group. These data show that Compound 23 does not impair teaming, but enhances learning in animals.

Method

Non-naive male Sprague Dawley rats (SASCO St. Louis) weighing between 2000–300 grams, were housed in groups of three in a temperature and humidity controlled vivarium having a 12 hour light/dark cycle. Animals had ad lib access to food and water.

Compound 23 was dissolved in 50% Polyethylene glycol (PEG) and administered in a dose range of 0.03–1.0 mg/kg. Clozapine was dissolved in 50% PEG and administered in a dose range of from 0.25 to 2 mg/kg. Both drugs were administered intravenously 5 minutes prior to trying in both learning tasks Apparatus:

Step-Down Passive Avoidance: A step-down passive avoidance platform 4 (cm)×7(cm) was placed in the center of an electrified gris floor, which was contained within a large (45×45×50 cm) white translucent plexiglas enclosure having a closable lid. The bars of the grip were spaced 1.5 cm apart and were wired to a BRS-LVE shock generator/scrambler which was set to deliver a 2 mA 6 second shock. Four passive avoidance boxes were automated by customer software (Labview) and commercial interface modules (National Instrments) connected to a computer. The timing and delivery of the shock as well as the latency to step down and the number of trials taken to reach criterion during training was under the control of the computer. All testing was done in the presence of 62 db white noise.

Modified Morris Water Maze: A water maze apparatus consisted of a circular tank (120 cm in diameter and 56 cm in height) having a black interior. The tank was surrounded by external visual cues which consisted of a black and white checkered wall, a black and white striped wall, a while wall and a blue panel. The tank was filled with water (18–20° C.) to a height of 52 cm and was divided into four quadrants (north, South, East and West). A black circular plexiglas platform (with black rubber top) was placed in the northeast quadrant approximately 1 cm below the surface of the water. The submerged platform was 51 cm in height and had a diameter of 9 cm. Training and testing was conducted in the presence of a 62 db white noise source and under dim light conditions.

Procedure:

1. Passive Avoidance:

Acquisition Training: After pretreatment with clozapine, Compound 23 or control (vehicle), the animal was placed on the platform which automatically started a timer. When the animal stepped off the platform it automatically received the footshock. Following each shock the animal was removed from the box and placed in its cage for a one minute intertrial interval and then returned to the platform. Training was terminated when the animal remained on the platform for 120 Seconds. Immediately after training the animal was returned to its home cage in a vivarium.

Retention Testing: Testing was conduced approximately 24 hours after training, Drug-free animals were placed on the platform in the box in which they were trained and the latency to step down onto the unshocked floor was recorded for one trial. The animal was allowed to a maximum of 120 seconds to step down.

2. Modified Morris Water Maze:

Acquisition Training: Acquisition training in this task assay consisted of either four or six training trials. The four trial procedure detects cognitive enhancing effects of drugs while the six trial procedure detects drugs that produce learning deficits in this task assay Compound 23 was tested in the water maze using a four rial procedure and clozapine using a six trial training procedure. Each animal was placed on the platform in the tank for 20 trials separated by an intertrial interval of 2 minutes. The starting position was pseudo-randomly varied but was the same order for each animal. During the ITI (intertrial interval) the animal was dried off and placed near a heat source (heat lamp). The latency to reach the submeged platform on each trial was measured and animals were allowed to remain on the platform for 10 seconds once they reach it. Since the platform was submerged just below the surface of the water, the animal was required to use the external visual cues surrounding the tank (distal cues) to locate the platform.

Retention Training: On the following day, each animal was individually tested for retention in one trial. All animals were placed in the "SOUTH" starting position and latency to find the submerged platform was recorded.

Results

Passive Avoidance: There were no significant differences for acquisition between the vehicle group and animals treated with Compound 23. Animals that received 0.25 mg/kg dose of Compound 23 remained on the platform for a significantly longer tirne during retest than the vehicle animals. Animals that received the 1.0 mg/kg and 2.0 mg/kg doses of clozapine showed a significant deficit in acquisition compared to the vehicle group. There were no significant differences in retention between clozapine treated animals and the vehicle group.

Water Maze: The difference between the first trial and the retest trial (latency to locate the platform on the following day) revealed significant improvement in retention relative to controls at the 0.03 mg/kd, 0.25 mg/kg and the 1.0 mg/kg dose of Compound 23. However, the difference between the scores of trial 1 and the retest trial for animals that received clozapine revealed no significant differences.

These results indicate that compound 23 improved memory in mammals. These results further show that compound 23 also enhances learning in mammals. Thus, the compounds of the invention are useful for enhancing cognition in mammals and can be used in methods for enhancing cognition, specifically learning and memory, in mammals.

The disclosures in this application of all articles and references, including patents, are incorporated herein by reference.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

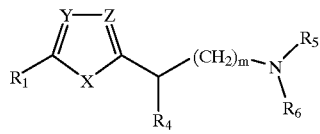

$R_1$ is aryl, heteroaryl, arylalkyl, cycloalkyl or napthyl; unsubstituted or substituted by up to 3 substituents which are the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $H_2$ or $NHCH_3$;

X is N or $NR_2$ where $R_2$ is hydrogen or methyl;

Y is N or $CR_3$

Z is $CR_3$ or N provided that Y and Z are not both $CR_3$; and
provided that Y and Z are not both N;

$R_3$ is hydrogen, lower alkyl, halogen, hydroxy, lower alkyl or phenyl unsubstituted or substituted by up to three substituents which are the same or different and represent hydrogen, halogen trifluoromethyl, cyano, sulfonamido, hydroxy, straight or branched chain lower alkyl having 1–6 carbon atoms, or straight or branched chain lower alkoxy having 1–6 carbon atoms;

$R_4$ is hydrogen or straight or branched chain lower alkyl having 1–6 carbon atoms, or $R_3$ and $R_4$ together represent —$(CH_2)_{n1}$— where n1 is 2, 3 or 4;

or $R_2$ and $R_4$ together represent —$(CH_2)_{n2}$— where n2 is 2, 3 or 4;

m is zero, one or two;

$R_5$ and $R_6$ are the same or different and represent hydrogen, straight or branched chain lower alkyl having 1–6 carbon atoms, aryl, straight or branched chain lower alkyl having 1–6 carbon atoms or $R_2$ and $R_5$ together represent —$(CH_2)_{n3}$— where n3 is 2 or 3; or $NR_5R_6$ together represent 2-(1,2,3,4-tetrahydroisoquionolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_5R_6$ represents

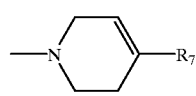

where $R_7$ is phenyl, benzyl, or phenethyl with the phenyl ring unsubstituted or substituted with up to three substituents which are the same or different and represent hydrogen, halogen, trifluoromethyl, hydroxy, straight or branched chain lower alkyl having 1–6 carbon atoms, or straight or branched chain lower alkoxy having 1–6 carbon atoms; or $NR_5R_6$ represents

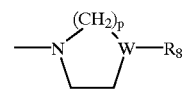

where p is 1, 2, or 3;
W is N or CH; and
W is N and $R_8$ is hydrogen, phenyl, pyridyl or pyrimidinyl, unsubstituted or mono or disubstituted with halogen, hydroxy, straight or branched lower alkyl having 1–6 carbon atoms, or straight or branched chain lower alkoxy having 1–6 carbon atoms; or
W is CH and $R_8$ is phenyl, or phenylalkyl each of which is unsubstituted or substituted at the phenyl ring with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

2. A pharmaceutical composition comprising a compound of the formula:

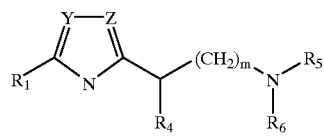

or a pharmaceutically acceptable salt thereof together with at least one pharmaceutically acceptable carrier, wherein $R_1$ is aryl, heteroaryl, arylalkyl, cycloalkyl or naphthyl; unsubstituted or substituted by up to 3 substituents which are the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$, where $R_9$ is $NH_2$ or $NHCH_3$;

X is N or $NR_2$ where $R_2$ is hydrogen or methyl;

Y is N or $CR_3$;

Z is $CR_3$ or N provided that Y and Z are not both $CR_3$; and
provided that Y and Z are not both N;

$R_3$ is hydrogen, lower alkyl, halogen, hydroxy lower alkyl or phenyl unsubstituted or substituted by up to three substituents which are the same or different and represent hydrogen, halogen, trifluoromethyl, cyano, sulfonamido, hydroxy, straight or branched chain lower alkyl having 1–6 carbon atoms, or straight or branched chain lower alkoxy having 1–6 carbon atoms;

$R_4$ is hydrogen or straight or branched chain lower alkyl having 1–6 carbon atoms or $R_3$ and $R_4$ together represent —$(CH_2)_{n1}$— where n1 is 2, 3, or 4; or $R_2$ and $R_4$ together represent —$(CH_2)_{n2}$ where n2 is 2, 3 or 4;

m is 0, 1, or 2;

$R_5$ and $R_6$ are the same or different and represent hydrogen, straight or branched chain lower alkyl having 1–6 carbon atoms, aryl straight or branched chain lower alkyl having 1–6 carbon atoms or $R_2$ and $R_5$ together represent —$(CH_2)_{n3}$— where n3 is 2 or 3; or $NR_5R_6$ together represent 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_5R_6$ represents

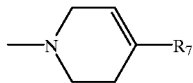

where $R_7$ is phenyl, benzyl or phenethyl with the phenyl ring unsubstituted or substituted with up to three substituents which are the same or different and represent hydrogen, halogen, trifluoromethyl, hydroxy, straight or branched chain lower alkyl having 1–6 carbon atoms, or straight or branched chain lower alkoxy having 1–6 carbon atoms; or $NR_5R_6$ represents

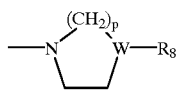

where p is 1, 2, or 3;
W is N or CH; and
W is N and $R_8$ is hydrogen, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or
W is CH and $R_8$ is phenyl or phenylalkyl each of which is unsubstituted or substituted at the phenyl ring with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

3. A pharmaceutical composition comprising a compound of the formula:

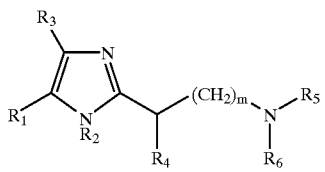

or a pharmaceutically acceptable salt thereof together with at least one pharmaceutically acceptable carrier, wherein $R_1$ is aryl, heteroaryl, arylalkyl, cycloalkyl or naphthyl; unsubstituted or substituted by up to 3 substituents which are the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$, where $R_9$ is $NH_2$ or $NHCH_3$;

$R_2$ is hydrogen or methyl;

$R_3$ is hydrogen, lower alkyl, halogen, hydroxy lower alkyl or phenyl unsubstituted or substituted by up to three substituents which are the same or different and represent hydrogen, halogen, trifluoromethyl, cyano, sulfonamido, hydroxy, straight or branched chain lower alkyl having 1–6 carbon atoms, or straight or branched chain lower alkoxy having 1–6 carbon atoms;

$R_4$ is hydrogen or straight or branched chain lower alkyl having 1–6 carbon atoms or $R_3$ and $R_4$ together represent —$(CH_2)_{n1}$— where n1 is 2, 3, or 4; or $R_2$ and $R_4$ together represent —$(CH_2)_{n2}$ where n2 is 2, 3, or 4;

m is 0, 1, or 2;

$R_5$ and $R_6$ are the same or different and represent hydrogen, straight or branched chain lower alkyl having 1–6 carbon atoms, aryl straight or branched chain lower alkyl having 1–6 carbon atoms or $R_2$ and $R_5$ together represent —$(CH_2)_{n3}$— where n3 is 2 or 3; or $NR_5R_6$ together represent 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_5R_6$ represents

where $R_7$ is phenyl, benzyl or phenethyl with the phenyl ring unsubstituted or substituted with up to three substituents which are the same or different and represent hydrogen, halogen, trifluoromethyl, hydroxy, straight or branched chain lower alkyl having 1–6 carbon atoms, or straight or branched chain lower alkoxy having 1–6 carbon atoms; or $NR_5R_6$ represents

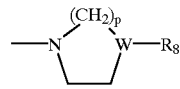

where p is 1, 2, or 3;
W is N or CH; and
W is N and $R_8$ is hydrogen, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or
W is CH and $R_8$ is phenyl or phenylalkyl each of which is unsubstituted or substituted at the phenyl ring with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

4. A pharmaceutical composition comprising a compound of claim 3, or a pharmaceutically acceptable salt thereof together with at least one pharmaceutically acceptable carrier, wherein $R_1$ is phenyl unsubstituted or mono or disubstituted with halogen or alkoxy;

$R_3$ is hydrogen;

$R_2$ and $R_4$ are hydrogen; and $R_5$ is alkyl and $R_6$ is arylalkyl; or $NR_5R_6$ is

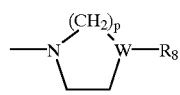

where p is 2.

5. A pharmaceutical composition comprising a compound of claim 3, or a pharmaceutically acceptable salt thereof together with at least one pharmaceutically acceptable carrier, wherein $R_1$ is phenyl unsubstituted or substituted with halogen or alkoxy;

$R_2$ and $R_4$ are hydrogen; and $NR_5R_6$ is

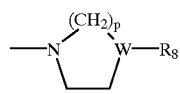

where p is 2;

W is N and $R_8$ is hydrogen, phenyl, pyridyl or pyrimidinyl, unsubstituted or mono or disubstituted with halogen, or straight or branched chain lower alkoxy having 1–6 carbon atoms.

6. A pharmaceutical composition comprising a compound of the formula:

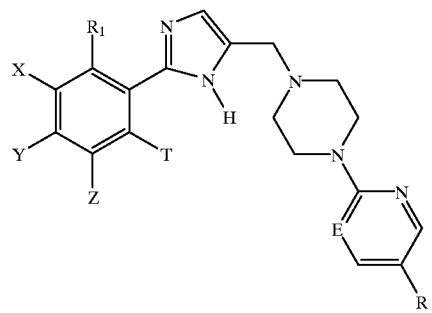

or a pharmaceutically acceptable salt thereof together with at least one pharmaceutically acceptable carrier, wherein R is halogen, alkoxy having 1–6 carbon atoms, or hydroxy;

$R_1$ and T independently represent hydrogen, halogen, hydroxy, lower alkyl, or lower alkoxy;

X, Y, and Z independently represent hydrogen, halogen, hydroxy, lower alkyl, lower alkoxy, or —$SO_2R_6$ where $R_6$ is lower alkyl; and E is CH or nitrogen.

7. A pharmaceutical composition comprising a compound of the formula:

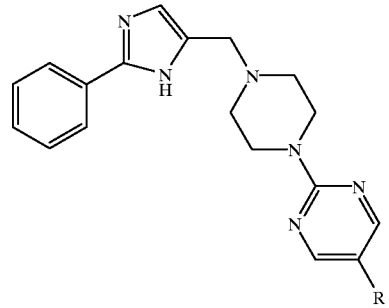

or a pharmaceutically acceptable salt thereof together with at least one pharmaceutically acceptable carrier, wherein R is halogen, alkoxy having 1–6 carbon atoms, or hydroxy; and E is CH or nitrogen.

8. A pharmaceutical composition comprising a compound of the formula:

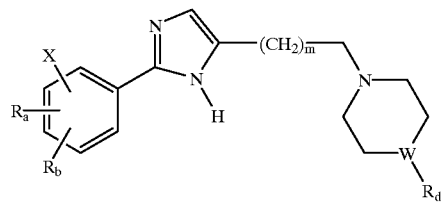

or a pharmaceutically acceptable salt thereof together with at least one pharmaceutically acceptable carrier, wherein R is halogen, alkoxy having 1–6 carbon atoms, or hydroxy.

9. A pharmaceutical composition comprising a compound of the formula:

or a pharmaceutically acceptable salt thereof together with at least one pharmaceutically acceptable carrier, wherein W is nitrogen, COH or CH;

$R_a$ and $R_b$ independently represent hydrogen or alkoxy;

X is halogen or hydrogen m is 0, 1, or 2; and $R_d$ is pyridyl, pyrimidinyl, phenylalkyl, or phenyl, each of which is unsubstituted or substituted with halogen, hydroxy, lower alkyl or lower alkoxy.

10. A pharmaceutical composition comprising a compound of the formula:

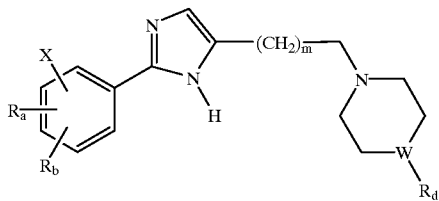

or a pharmaceutically acceptable salt thereof together with at least one pharmaceutically acceptable carrier, wherein W is CH or COH;

$R_a$ and $R_b$ independently represent hydrogen or alkoxy;

X is halogen or hydrogen m is 0, 1, or 2; and $R_d$ is pyridyl, pyrimidinyl, phenylalkyl, or phenyl, each of which is unsubstituted or substituted with halogen, hydroxy, lower alkyl or lower alkoxy.

11. A pharmaceutical composition comprising a compound of the formula:

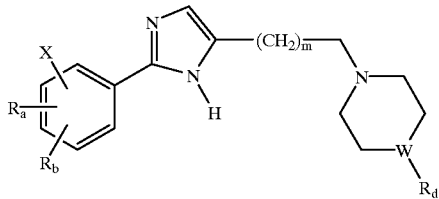

or a pharmaceutically acceptable salt thereof together with at least one pharmaceutically acceptable carrier, wherein $R_a$ and $R_b$ independently represent hydrogen or alkoxy;

X is halogen or hydrogen;

m is 0, 1, or 2; and $R_d$ is pyridyl, pyrimidinyl, phenylalkyl, or phenyl, each of which is unsubstituted or substituted with halogen, hydroxy lower alkyl or lower alkoxy.

12. A pharmaceutical composition comprising a compound according to claim 1 combined with at least one pharmaceutically acceptable carrier or excipient.

13. A pharmaceutical composition according to claim 1 wherein the compound is selected from the group consisting of 2-Phenyl-4(5)-4-(5-hydroxypyrimidin-2-yl)piperazin-1-yl)methylimidazole;

2-Phenyl-4(5)-4-(5-fluoropyrimidin-2-yl)piperazin-1-yl) methylimidazole; and

2-Phenyl-4(5)-4-(5-methoxypyrimidin-2-yl)piperazin-1-yl)methylimidazole.

14. A method for treatment of schizophrenia, which comprises administering to a patient in need of such treatment a therapeutically effective amount of a compound of the formula:

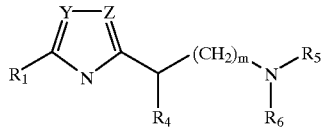

or a pharmaceutically acceptable salt thereof, wherein $R_1$ is aryl, heteroaryl, arylalkyl, cycloalkyl or naphthyl;

unsubstituted or substituted by up to 3 substituents which are the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$, where $R_9$ is $NH_2$ or $NHCH_3$;

X is N or $NR_2$ where $R_2$ is hydrogen or straight or branched chain lower alkyl having 1–6 carbon atoms;

Y is N or $CR_3$;

Z is $CR_3$ or N provided that Y and Z are not both $CR_3$; and provided that Y and Z are not both N;

$R_3$ is hydrogen, lower alkyl, halogen, hydroxy lower alkyl or phenyl unsubstituted or substituted by up to three substituents which are the same or different and represent hydrogen, halogen, trifluoromethyl, cyano, sulfonamido, hydroxy, straight or branched chain lower alkyl having 1–6 carbon atoms, or straight or branched chain lower alkoxy having 1–6 carbon atoms;

$R_4$ is hydrogen or straight or branched chain lower alkyl having 1–6 carbon atoms or $R_3$ and $R_4$ together may represent $-(CH_2)_{n1}-$ where n1 is 2, 3, or 4; or $R_2$ and $R_4$ together may represent $-(CH_2)_{n2}$ where n2 is 2, 3, or 4;

m is 0, 1, or 2;

$R_5$ and $R_6$ are the same or different and represent hydrogen, straight or branched chain lower alkyl having 1–6 carbon atoms, aryl straight or branched chain lower alkyl having 1–6 carbon atoms or $R_2$ and $R_5$ together represent $-(CH_2)_{n3}-$ where n3 is 2 or 3; or $NR_5R_6$ together represent 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_5R_6$ represents

where $R_7$ is phenyl, benzyl or phenethyl with the phenyl ring unsubstituted or substituted with up to three substituents which may be the same or different and represent hydrogen, halogen, trifluoromethyl, hydroxy, straight or branched chain lower alkyl having 1–6 carbon atoms, or straight or branched chain lower alkoxy having 1–6 carbon atoms; or $NR_5R_6$ represents

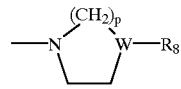

where p is 1, 2, or 3;

W is N or CH; and

W is N and $R_8$ is hydrogen, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or W is CH and $R_8$ is phenyl or phenylalkyl each of which is unsubstituted or substituted at the phenyl ring with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

15. A method for treatment of depression, which comprises administering to a patient in need of such treatment a therapeutically effective amount of a compound of the formula:

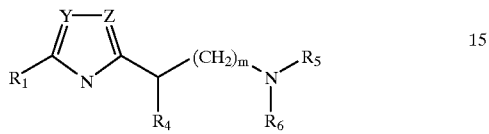

or a pharmaceutically acceptable salt thereof, wherein $R_1$ is aryl, heteroaryl, arylalkyl, cycloalkyl or naphthyl; unsubstituted or substituted by up to 3 substituents which may be the same or different and represent hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$, where $R_9$ is $NH_2$ or $NHCH_3$;

X is N or $NR_2$ where $R_2$ is hydrogen or straight or branched chain lower alkyl having 1–6 carbon atoms;

Y is N or $CR_3$;

Z is $CR_3$ or N
provided that Y and Z are not both $CR_3$; and
provided that Y and Z are not both N;

$R_3$ is hydrogen, lower alkyl, halogen, hydroxy lower alkyl or phenyl unsubstituted or substituted by up to three substituents which are the same or different and represent hydrogen, halogen, trifluoromethyl, cyano, sulfonamido, hydroxy, straight or branched chain lower alkyl having 1–6 carbon atoms, or straight or branched chain lower alkoxy having 1–6 carbon atoms;

$R_4$ is hydrogen or straight or branched chain lower alkyl having 1–6 carbon atoms or $R_3$ and $R_4$ together represent —$(CH_2)_{n1}$— where n1 is 2, 3, or 4; or $R_2$ and $R_4$ together represent —$(CH_2)_{n2}$ where n2 is 2, 3, or 4;

m is 0, 1, or 2;

$R_5$ and $R_6$ are the same or different and represent hydrogen, straight or branched chain lower alkyl having 1–6 carbon atoms, aryl straight or branched chain lower alkyl having 1–6 carbon atoms or $R_2$ and $R_5$ together represent —$(CH_2)_{n3}$— where n3 is 2 or 3; or $NR_5R_6$ together represent 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or $NR_5R_6$ represents

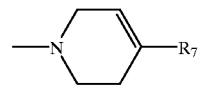

where $R_7$ is phenyl, benzyl or phenethyl with the phenyl ring unsubstituted or substituted with up to three substituents which may be the same or different and represent hydrogen, halogen, trifluoromethyl, hydroxy, straight or branched chain lower alkyl having 1–6 carbon atoms, or straight or branched chain lower alkoxy having 1–6 carbon atoms; or $NR_5R_6$ represents

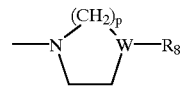

where p is 1, 2, or 3;
W is N or CH; and
W is N and $R_8$ is hydrogen, phenyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; or W is CH and $R_8$ is phenyl or phenylalkyl each of which is unsubstituted or substituted at the phenyl ring with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

16. A method for treatment of schizophrenia, which comprises administering to a patient in need of such treatment a therapeutically effective amount of a compound of the formula:

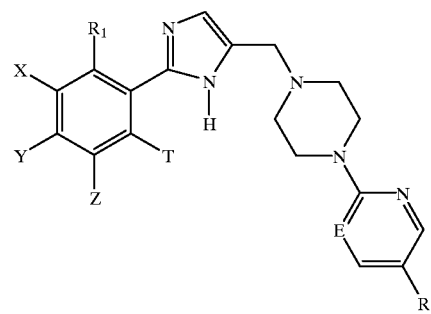

or a pharmaceutically acceptable salt thereof, wherein
R is halogen, alkoxy having 1–6 carbon atoms, or hydroxy;
$R_1$ and T independently represent hydrogen, halogen, hydroxy, lower alkyl, or lower alkoxy;
X, Y, and Z independently represent hydrogen, halogen, hydroxy, lower alkyl, lower alkoxy, or —$SO_2R_6$ where $R_6$ is lower alkyl; and
E is CH or nitrogen.

17. A method for treatment of depression, which comprises administering to a patient in need of such treatment a therapeutically effective amount of a compound of the formula:

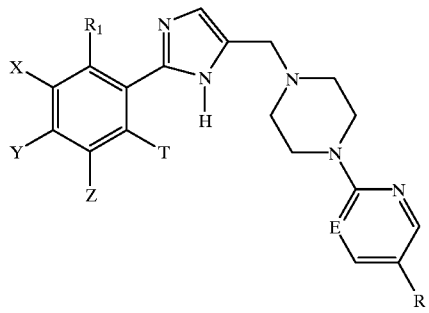

or a pharmaceutically acceptable salt thereof, wherein
  R is halogen, alkoxy having 1–6 carbon atoms, or hydroxy;
  $R_1$ and T independently represent hydrogen, halogen, hydroxy, lower alkyl, or lower alkoxy;
  X, Y, and Z independently represent hydrogen, halogen, hydroxy, lower alkyl, lower alkoxy, or —$SO_2R_6$ where $R_6$ is lower alkyl; and
  E is CH or nitrogen.

18. A method for treatment of schizophrenia, which comprises administering to a patient in need of such treatment a therapeutically effective amount of a compound of the formula:

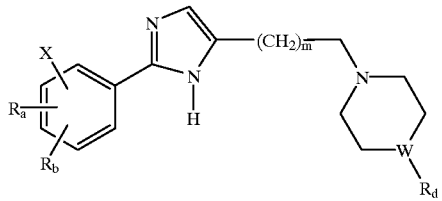

or a pharmaceutically acceptable salt thereof, wherein
  W is nitrogen, COH or CH;
  $R_a$ and $R_b$ independently represent hydrogen or alkoxy;
  X is halogen or hydrogen
  m is 0, 1, or 2; and
  $R_d$ is pyridyl, pyrimidinyl, phenylalkyl, or phenyl, each of which is unsubstituted or substituted with halogen, hydroxy, lower alkyl or lower alkoxy.

19. A method for treatment of depression, which comprises administering to a patient in need of such treatment a therapeutically effective amount of a compound of the formula:

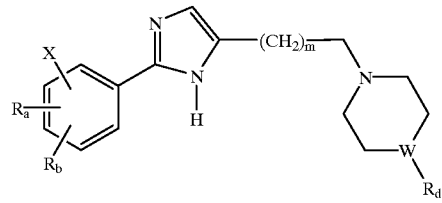

or a pharmaceutically acceptable salt thereof, wherein
  W is nitrogen, COH or CH;
  $R_a$ and $R_b$ independently represent hydrogen or alkoxy;
  X is halogen or hydrogen
  m is 0, 1, or 2; and
  $R_d$ is pyridyl, pyrimidinyl, phenylalkyl, or phenyl, each of which is unsubstituted or substituted with halogen, hydroxy, lower alkyl or lower alkoxy.

20. A compound of the formula:

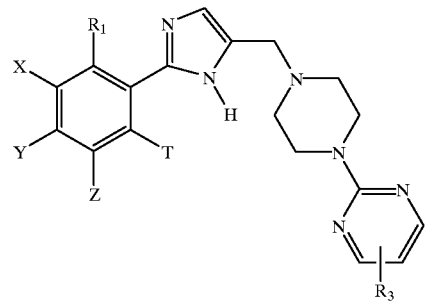

or a pharmaceutically acceptable salt thereof, wherein:
  R and T independently present hydrogen, halogen, hydroxy, lower alkyl having from 1–6 carbon atoms, or lower alkoxy having from 1–6 carbon atoms;
  X, Y, and Z independently represent hydrogen, halogen, hydroxy, lower alkyl having from 1–6 carbon atoms, or lower alkoxy having from 1–6 carbon atoms, or $SO_2R_3$, where $R_3$ is lower alkyl having from 1–6 carbon atoms,
  $R_1$ is hydrogen or methyl; and
  $R_3$ is halogen, hydroxy, lower alkyl having from 1–6 carbon atoms, or lower alkoxy having from 1–6 carbon atoms.

21. A pharmaceutical composition according to claim 9 wherein the compound is selected from the group consisting of
  2-phenyl-4(5)-(4-(2-pyrimidinyl)-piperazin-1-yl)-propan-1-yl-imidazole;
  2-phenyl-4(5)-(4-phenyl-piperazin-1-yl)-propan-1-yl-imidazole; and
  2-phenyl-4(5)-(4-hydroxy-4-(4-chlorophenyl)-piperidin-1-yl)-propan-1-yl-imidazole.

* * * * *